(12) United States Patent
Chou et al.

(10) Patent No.: US 11,712,177 B2
(45) Date of Patent: Aug. 1, 2023

(54) ASSAY WITH TEXTURED SURFACE

(71) Applicant: Essenlix Corporation, Monmouth Junction, NJ (US)

(72) Inventors: Stephen Y. Chou, Princeton, NJ (US); Wei Ding, East Windsor, NJ (US); Yufan Zhang, Monmouth Junction, NJ (US); Ji Qi, Hillsborough, NJ (US)

(73) Assignee: Essenlix Corporation, Monmouth Junction, NJ (US)

( * ) Notice: Subject to any disclaimer, the term of this patent is extended or adjusted under 35 U.S.C. 154(b) by 0 days.

(21) Appl. No.: 17/016,298

(22) Filed: Sep. 9, 2020

(65) Prior Publication Data

US 2021/0045658 A1 Feb. 18, 2021

Related U.S. Application Data

(63) Continuation of application No. 16/485,347, filed on Aug. 12, 2019, now Pat. No. 10,966,634.

(51) Int. Cl.
*A61B 5/097* (2006.01)
*A61B 5/00* (2006.01)
(Continued)

(52) U.S. Cl.
CPC ............ *A61B 5/097* (2013.01); *A61B 5/0022* (2013.01); *A61B 5/0833* (2013.01);
(Continued)

(58) Field of Classification Search
CPC ....... G01N 2035/0081; G01N 21/6428; G01N 2021/6419; G01N 2021/6421; G01N 2021/6441; G01N 15/1434; G01N 15/1484; G01N 15/14; G01N 15/1436; G01N 2015/149; G01N 15/147; G01N 2015/0065; G01N 2015/1497; G01N 2015/1006; G01N 15/1459; G01N 15/1427; G01N 15/1429; G01N 15/1463; G01N 21/1702; G01N 21/3563; G01N 2201/0612; G01N 29/2418; G01N 15/1475; G01N 21/648; G01N 2015/1481; G01N 2015/1493; G01N 2021/653; G01N 21/35; G01N 21/65; G01N 2035/0436; G01N 35/026; G01N 2291/02466; G01N 2035/0425; G01N 21/658; G01N 21/645; G01N 21/6486; G01N 33/54373; G01N 33/54386;
(Continued)

(56) References Cited

U.S. PATENT DOCUMENTS 4,110,079 A * 8/1978 Schaeffer ............. G01N 33/525
422/423
5,451,500 A 9/1995 Stapleton et al.
(Continued)

FOREIGN PATENT DOCUMENTS

CA 2318881 A1 * 8/1999
CA 3053301 A1 * 8/2018 ........... A61B 5/0022
(Continued)

*Primary Examiner* — Michael P Stafira

(57) ABSTRACT

Among other thing, the present invention provides solution to the problem, particularly, the present invention certain surfaces and certain sample holder to improve the sensitivity, speed, and easy-to-use of an optical signal based assays, such as colorimetric assays or fluorescence assays.

35 Claims, 13 Drawing Sheets

(51) Int. Cl.

| | | |
|---|---|---|
| *G01N 1/22* | (2006.01) | |
| *G01N 1/30* | (2006.01) | |
| *G01N 1/31* | (2006.01) | |
| *G01N 33/543* | (2006.01) | |
| *G01N 33/497* | (2006.01) | |
| *G16H 10/40* | (2018.01) | |
| *G16H 40/67* | (2018.01) | |
| *A61B 5/083* | (2006.01) | |
| *B01L 3/00* | (2006.01) | |
| *G01N 21/01* | (2006.01) | |
| *G01N 21/27* | (2006.01) | |
| *G01N 21/64* | (2006.01) | |
| *G01N 21/78* | (2006.01) | |
| *G06Q 40/08* | (2012.01) | |
| *G01N 21/17* | (2006.01) | |

(52) U.S. Cl.
CPC ............ *A61B 5/0836* (2013.01); *B01L 3/508* (2013.01); *G01N 1/22* (2013.01); *G01N 1/30* (2013.01); *G01N 1/31* (2013.01); *G01N 21/01* (2013.01); *G01N 21/272* (2013.01); *G01N 21/645* (2013.01); *G01N 21/78* (2013.01); *G01N 33/497* (2013.01); *G01N 33/54306* (2013.01); *G01N 33/54386* (2013.01); *G16H 10/40* (2018.01); *G16H 40/67* (2018.01); *B01L 2300/0654* (2013.01); *B01L 2300/0816* (2013.01); *B01L 2300/0851* (2013.01); *B01L 2300/123* (2013.01); *B01L 2300/168* (2013.01); *B01L 2400/0406* (2013.01); *G01N 21/17* (2013.01); *G01N 2001/2244* (2013.01); *G01N 2001/302* (2013.01); *G01N 2021/1776* (2013.01); *G01N 2033/4975* (2013.01); *G06Q 40/08* (2013.01)

(58) Field of Classification Search
CPC ......... G01N 1/2813; G01N 2021/7786; G01N 21/0303; G01N 21/01; G01N 21/7703; G01N 21/78; G01N 2201/06113; G01N 2001/2244; G01N 2033/4975; G01N 21/03; G01N 21/25; G01N 21/6452; G01N 2201/0221; G01N 33/497; G01N 1/22; G01N 1/30; G01N 1/31; G01N 2001/302; G01N 2015/1454; G01N 2021/035; G01N 2021/036; G01N 2021/1776; G01N 2021/3595; G01N 2021/6439; G01N 2021/6482; G01N 21/17; G01N 21/272; G01N 21/3577; G01N 21/532; G01N 21/6458; G01N 2201/0662; G01N 2201/12; G01N 2201/1288; G01N 33/487; G01N 33/49; G01N 33/54306; G01N 1/2214; G01N 1/2247; G01N 2001/282; G01N 2021/0346; G01N 2021/6463; G01N 2035/103; G01N 21/64; G01N 21/7743; G01N 2201/08; G01N 27/44704; G01N 33/54393; G01N 33/545; G01N 33/553; G01N 2021/3122; G01N 2021/7753; G01N 21/255; G01N 21/554; G01N 21/6454; G01N 21/77; G01N 2201/0642; G01N 2610/00; G01N 33/542; G01N 33/54366; G01N 21/05; G01N 21/274; G01N 21/553; G01N 33/483; G01N 33/552; G01N 33/588; G01N 1/28; G01N 1/286; G01N 15/1456; G01N 15/1468; G01N 2001/2276; G01N 2001/4016; G01N 2015/1438; G01N 2015/144; G01N 2015/145; G01N 2015/1486; G01N 2021/0118; G01N 2021/0181; G01N 21/31; G01N 21/3103; G01N 21/359; G01N 21/636; G01N 21/6456; G01N 21/76; G01N 2333/726; G01N 2458/00; G01N 2496/05; G01N 2500/02; G01N 2500/04; G01N 27/305; G01N 27/3272; G01N 27/44726; G01N 27/44782; G01N 31/22; G01N 33/02; G01N 33/4833; G01N 33/5094; G01N 33/53; G01N 33/5308; G01N 33/543; G01N 33/54313; G01N 33/56966; G01N 33/58; G01N 33/582; G01N 33/583; G01N 33/587; G01N 33/60; G01N 33/6845; G01N 33/6896; G01N 33/74; A61B 5/0836; A61B 5/097; A61B 5/0022; A61B 5/0833; A61B 5/1455; A61B 5/1495; A61B 8/08; A61B 2562/0295; A61B 2562/146; A61B 5/00; A61B 5/0071; A61B 5/082; A61B 5/0935; A61B 5/1032; A61B 5/14532; A61B 5/14546; A61B 5/6826; A61B 5/6838; A61B 5/6898; G16H 10/40; G16H 40/67; G16H 50/30; B01L 2200/16; B01L 2200/10; B01L 2300/0816; B01L 2300/0887; B01L 7/52; B01L 2300/1822; B01L 2200/148; B01L 2300/1827; B01L 2300/1861; B01L 2400/0481; B01L 2200/027; B01L 2200/147; B01L 2300/021; B01L 2300/045; B01L 2300/0681; B01L 2300/0867; B01L 2300/087; B01L 2400/0442; B01L 2400/0487; B01L 2400/0611; B01L 2400/0677; B01L 2400/0683; B01L 9/527; B01L 3/502715; B01L 3/502738; B01L 3/502723; B01L 3/5027; B01L 2300/0627; B01L 3/502761; B01L 3/5085; B01L 2300/0636; B01L 2300/0819; B01L 3/5088; B01L 2200/0642; B01L 2200/06; B01L 2400/0409; B01L 3/50851; B01L 2200/0652; B01L 2300/0864; B01L 2200/0636; B01L 9/06; B01L 2300/06; B01L 2300/0832; B01L 2300/18; B01L 3/0275; B01L 3/52; B01L 2300/0822; B01L 2300/0851; B01L 2300/168; B01L 2300/123; B01L 2400/0406; B01L 2200/12; B01L 2300/0654; B01L 3/508; B01L 2200/143; B01L 2300/0893; B01L 2300/1811; B01L 3/0241; B01L 2200/021; B01L 2200/025; B01L 2200/0689; B01L 2300/1805; B01L 2400/0655; B01L 2200/142; B01L 2300/046; B01L 2300/048; B01L 2300/049; B01L 2300/0645; B01L 2300/0809; B01L 2300/0825; B01L 3/502; B01L 3/5023; B01L 3/502707; B01L 3/50853

See application file for complete search history.

(56) References Cited

U.S. PATENT DOCUMENTS

| | | |
|---|---|---|
| 6,017,767 A | 1/2000 | Chandler |
| 6,358,475 B1 | 3/2002 | Berndt |
| 6,623,701 B1 | 9/2003 | Eichele et al. |
| 7,384,792 B1 | 6/2008 | Wang et al. |

(56) References Cited

U.S. PATENT DOCUMENTS

| | | |
|---|---|---|
| 7,405,054 B1 | 7/2008 | Hasenbank et al. |
| 7,468,160 B2 | 12/2008 | Thompson et al. |
| 7,850,916 B2 | 12/2010 | Wardlaw |
| 8,326,008 B2 | 12/2012 | Lalpuria |
| 8,633,013 B2 | 1/2014 | Kaiser et al. |
| 8,911,815 B2 | 12/2014 | Kram et al. |
| 9,084,995 B2 | 7/2015 | Wardlaw |
| 2002/0126271 A1 | 9/2002 | Berndt |
| 2002/0164820 A1 | 11/2002 | Brown |
| 2003/0068614 A1 | 4/2003 | Cima et al. |
| 2003/0180191 A1 | 9/2003 | Suzuki et al. |
| 2004/0131345 A1 | 7/2004 | Kylberg et al. |
| 2005/0000811 A1 | 1/2005 | Luka |
| 2005/0036667 A1 | 2/2005 | So et al. |
| 2005/0233352 A1 | 10/2005 | Zoval |
| 2006/0011860 A1 | 1/2006 | Hecht et al. |
| 2006/0051253 A1 | 3/2006 | Gausepohl |
| 2006/0062440 A1 | 3/2006 | Hollars et al. |
| 2006/0154248 A1 | 7/2006 | McGrew et al. |
| 2008/0286152 A1 | 11/2008 | Schmidt et al. |
| 2009/0079978 A1 | 3/2009 | Kimura |
| 2009/0211344 A1 | 8/2009 | Wang |
| 2009/0261269 A1 | 10/2009 | Horii et al. |
| 2010/0034699 A1 | 2/2010 | Chan |
| 2010/0216248 A1 | 8/2010 | Wardlaw |
| 2011/0009163 A1 | 1/2011 | Fletcher et al. |
| 2011/0092389 A1 | 4/2011 | Dickinson et al. |
| 2011/0212462 A1 | 9/2011 | Duffy et al. |
| 2011/0305842 A1 | 12/2011 | Kram |
| 2012/0108787 A1 | 5/2012 | Lue |
| 2012/0157160 A1 | 6/2012 | Ozcan et al. |
| 2012/0321518 A1 | 12/2012 | Ermantraut et al. |
| 2013/0008789 A1 | 1/2013 | Ronaghi et al. |
| 2013/0052331 A1 | 2/2013 | Kram et al. |
| 2013/0065788 A1 | 3/2013 | Glezer et al. |
| 2013/0184188 A1 | 7/2013 | Ewart et al. |
| 2013/0265054 A1 | 10/2013 | Lowery, Jr. et al. |
| 2013/0300919 A1 | 11/2013 | Fletcher |
| 2013/0309679 A1 | 11/2013 | Ismagilov et al. |
| 2013/0331298 A1 | 12/2013 | Rea |
| 2014/0264082 A1 | 9/2014 | Ayliffe |
| 2014/0353157 A1 | 12/2014 | Hoffmeyer et al. |
| 2014/0369386 A1 | 12/2014 | Radhakrishnan et al. |
| 2014/0378320 A1 | 12/2014 | Hoffmann et al. |
| 2015/0233910 A1 | 8/2015 | Miller et al. |
| 2015/0241353 A1 | 8/2015 | Oki et al. |
| 2015/0253321 A1 | 9/2015 | Chou et al. |
| 2016/0003814 A1 | 1/2016 | Hamasaki et al. |
| 2016/0004057 A1 | 1/2016 | Lin et al. |
| 2017/0021356 A1 | 1/2017 | Dority et al. |
| 2017/0261435 A1 | 9/2017 | Oyama et al. |
| 2019/0170734 A1* | 6/2019 | Chou ................. G01N 21/6486 |
| 2019/0220679 A1* | 7/2019 | Chou ..................... G06V 10/40 |
| 2020/0033579 A1* | 1/2020 | Chou ............... G01N 33/54386 |

FOREIGN PATENT DOCUMENTS

| | | | |
|---|---|---|---|
| EP | 0961110 A2 | 12/1999 | |
| JP | 2016057179 A | 4/2016 | |
| JP | 2016116485 A | 6/2016 | |
| WO | WO-0161357 A2 * | 8/2001 | ............. B82Y 30/00 |
| WO | WO-2004055198 A2 * | 7/2004 | ............ B01L 3/5027 |
| WO | WO-2005043123 A2 * | 5/2005 | ............. C08J 7/047 |
| WO | 2006135437 A2 | 12/2006 | |
| WO | 2008022332 A2 | 2/2008 | |
| WO | 2008128352 A1 | 10/2008 | |
| WO | 2014121388 A1 | 8/2014 | |
| WO | WO-2014118778 A1 * | 8/2014 | ............... C09D 1/00 |
| WO | 2014144133 A1 | 9/2014 | |
| WO | WO-2017048871 A1 * | 3/2017 | ............ B01L 3/5055 |
| WO | WO-2017048881 A1 * | 3/2017 | ............ A61B 5/0836 |
| WO | WO-2017070577 A1 * | 4/2017 | ......... B01J 19/0046 |
| WO | WO-2017156308 A1 * | 9/2017 | ............ G01N 33/531 |
| WO | WO-2018148609 A2 * | 8/2018 | ........ B01L 3/502715 |
| WO | WO-2018152421 A1 * | 8/2018 | ............ A61B 5/0022 |
| WO | WO-2018152422 A1 * | 8/2018 | ............ A61B 5/0022 |

* cited by examiner

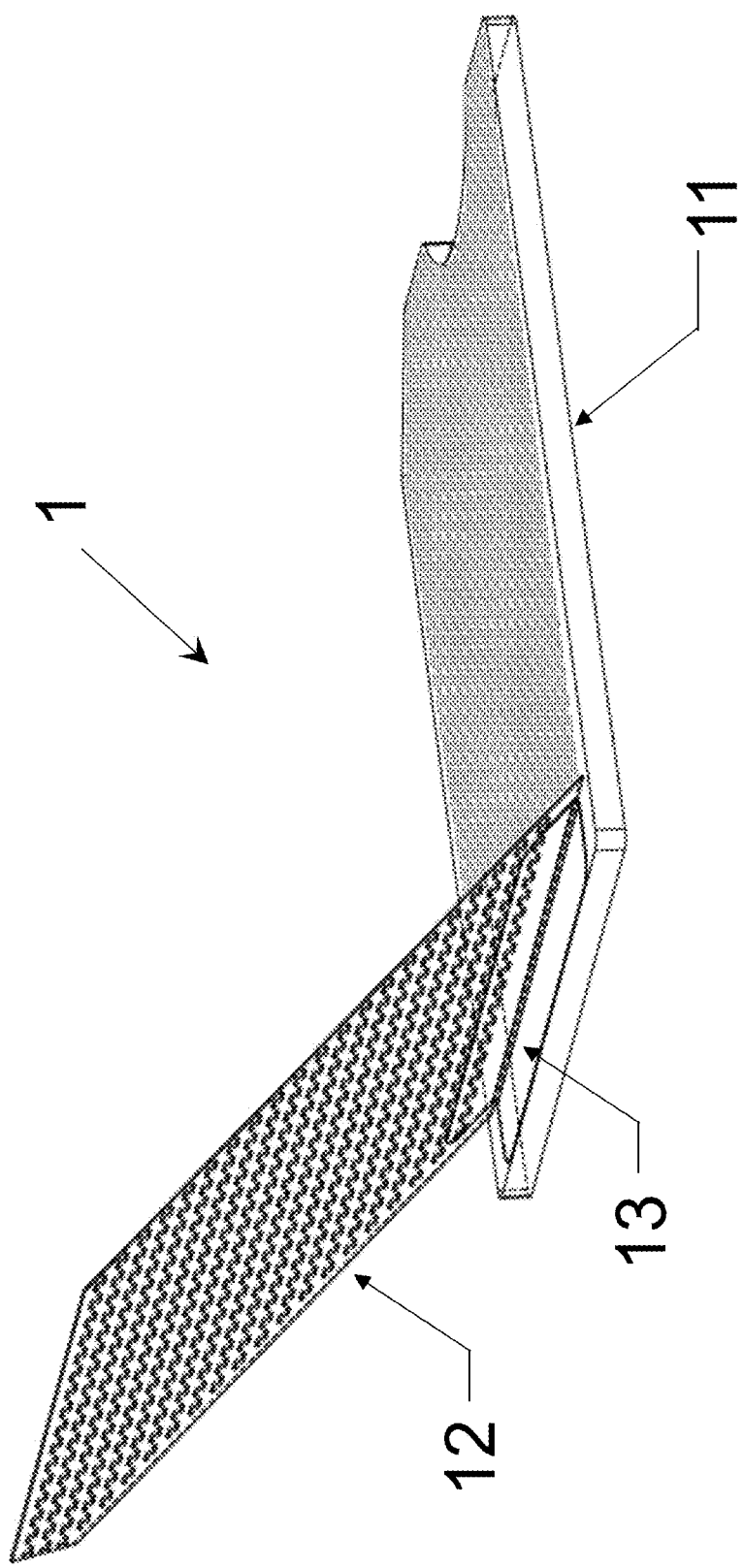

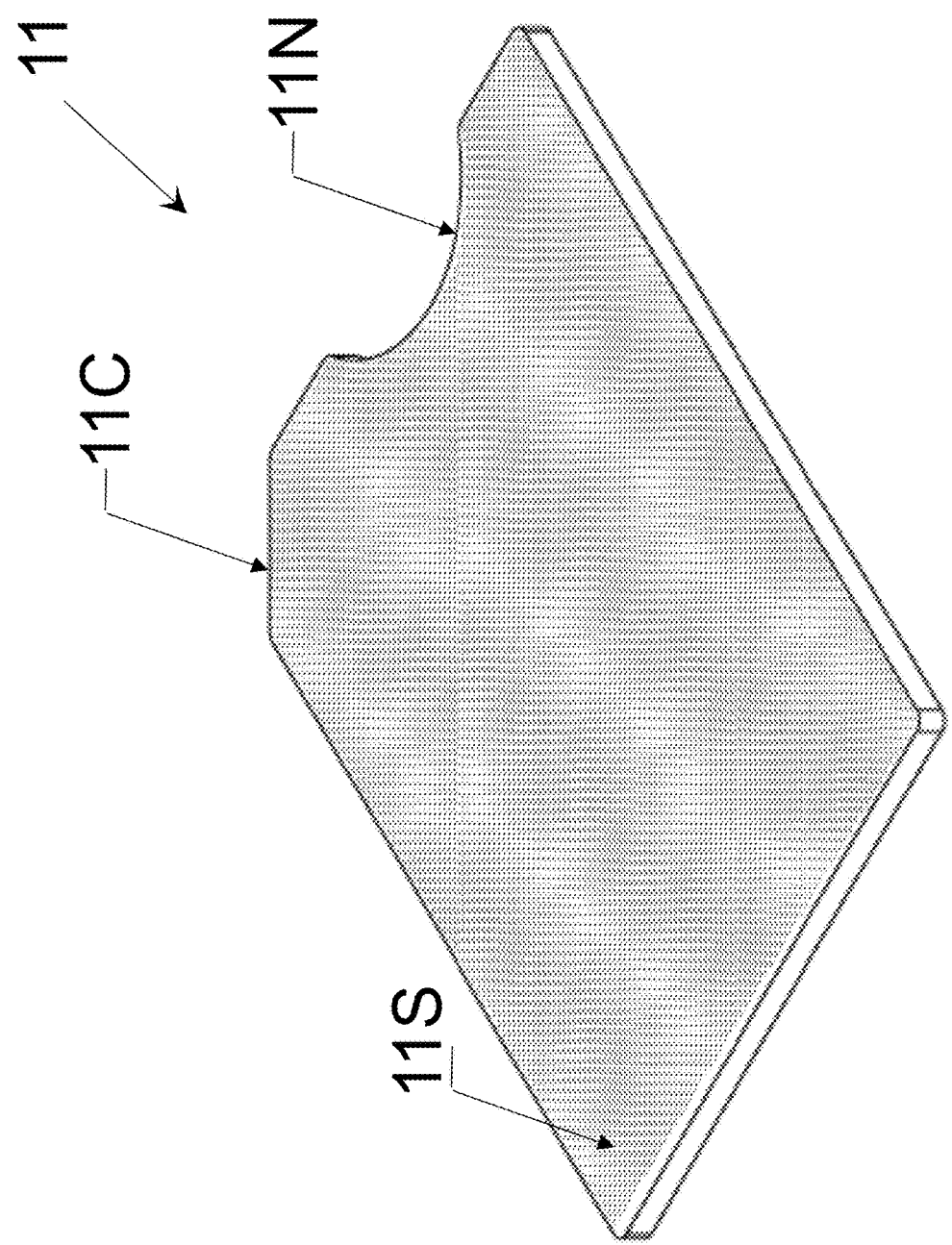
Fig. 1-B

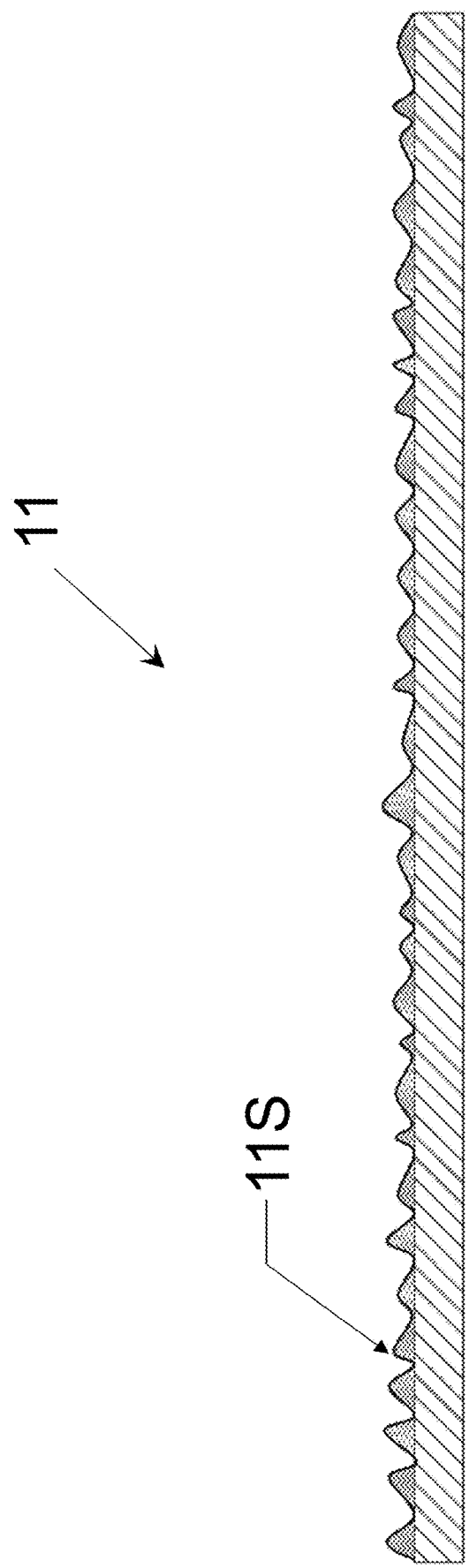
Fig. 1-C

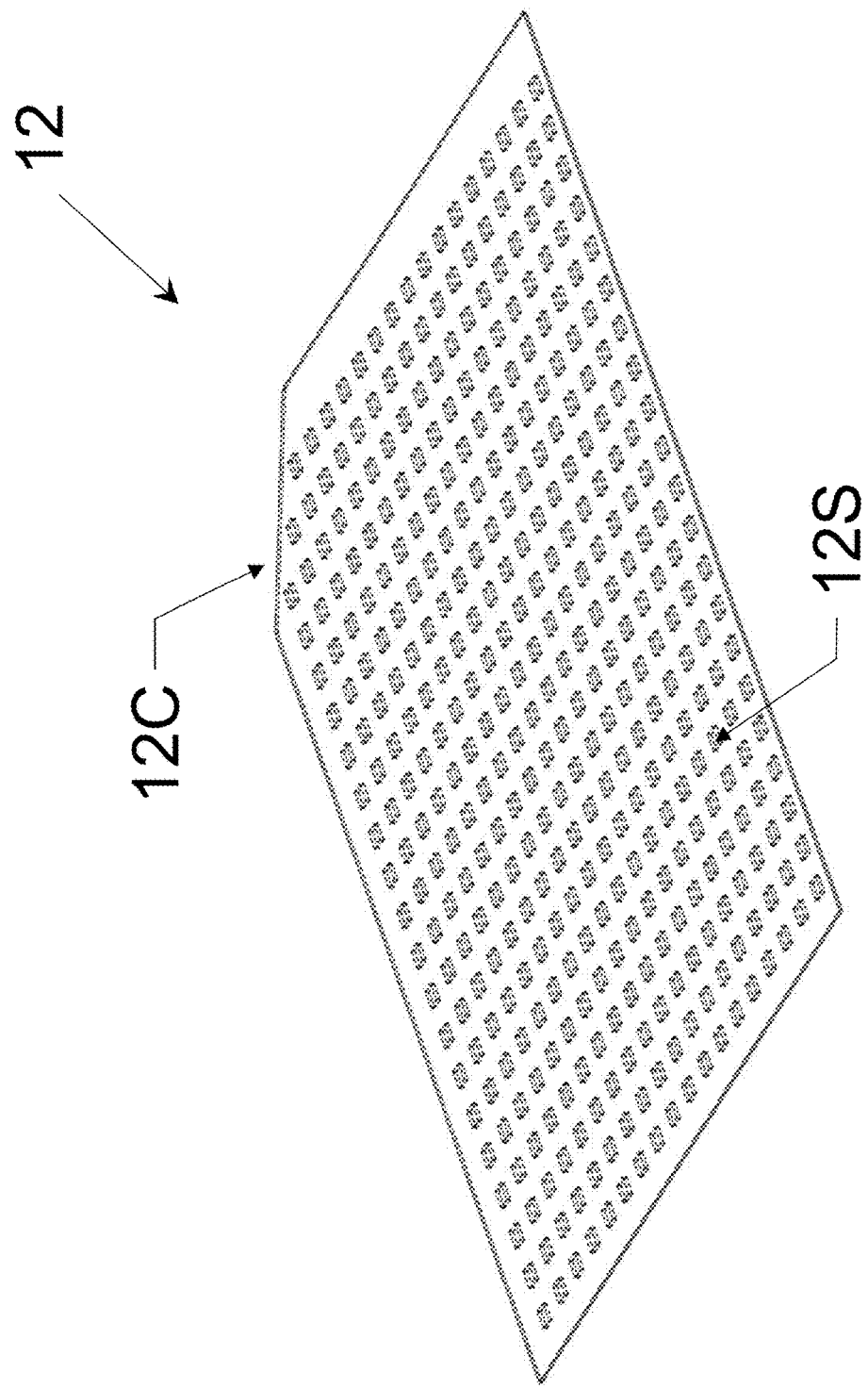
Fig. 1-D

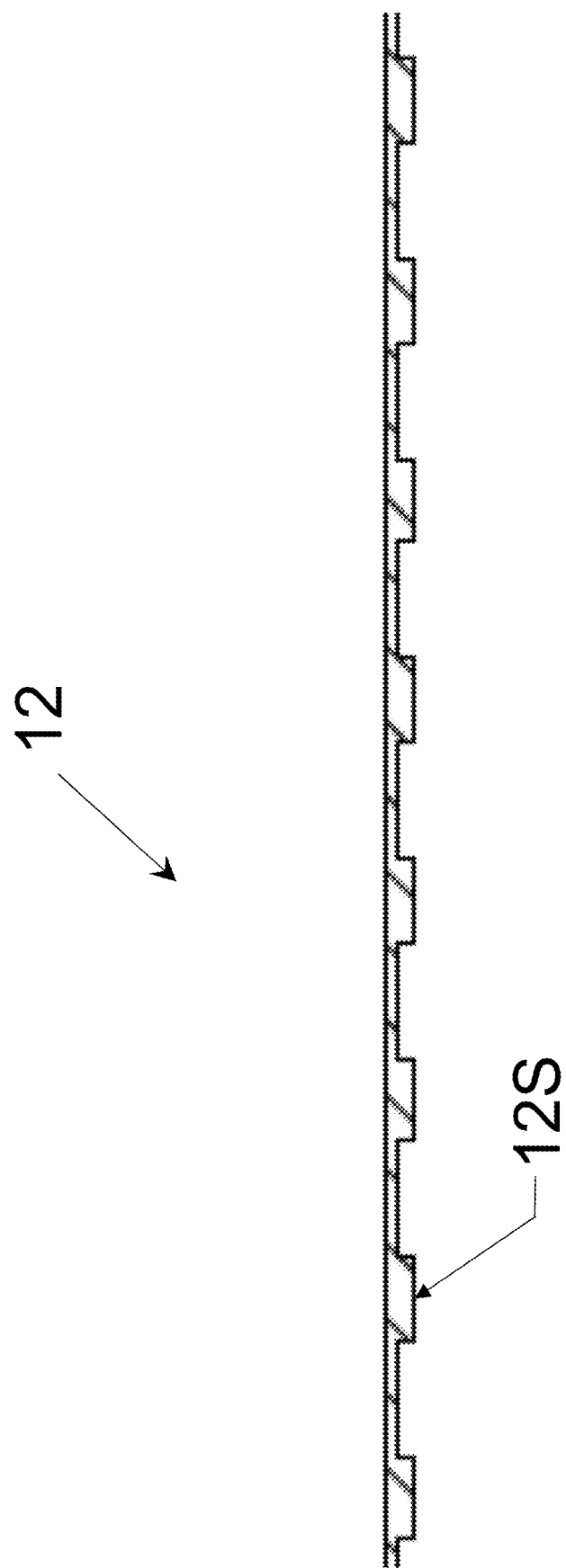
Fig. 1-E

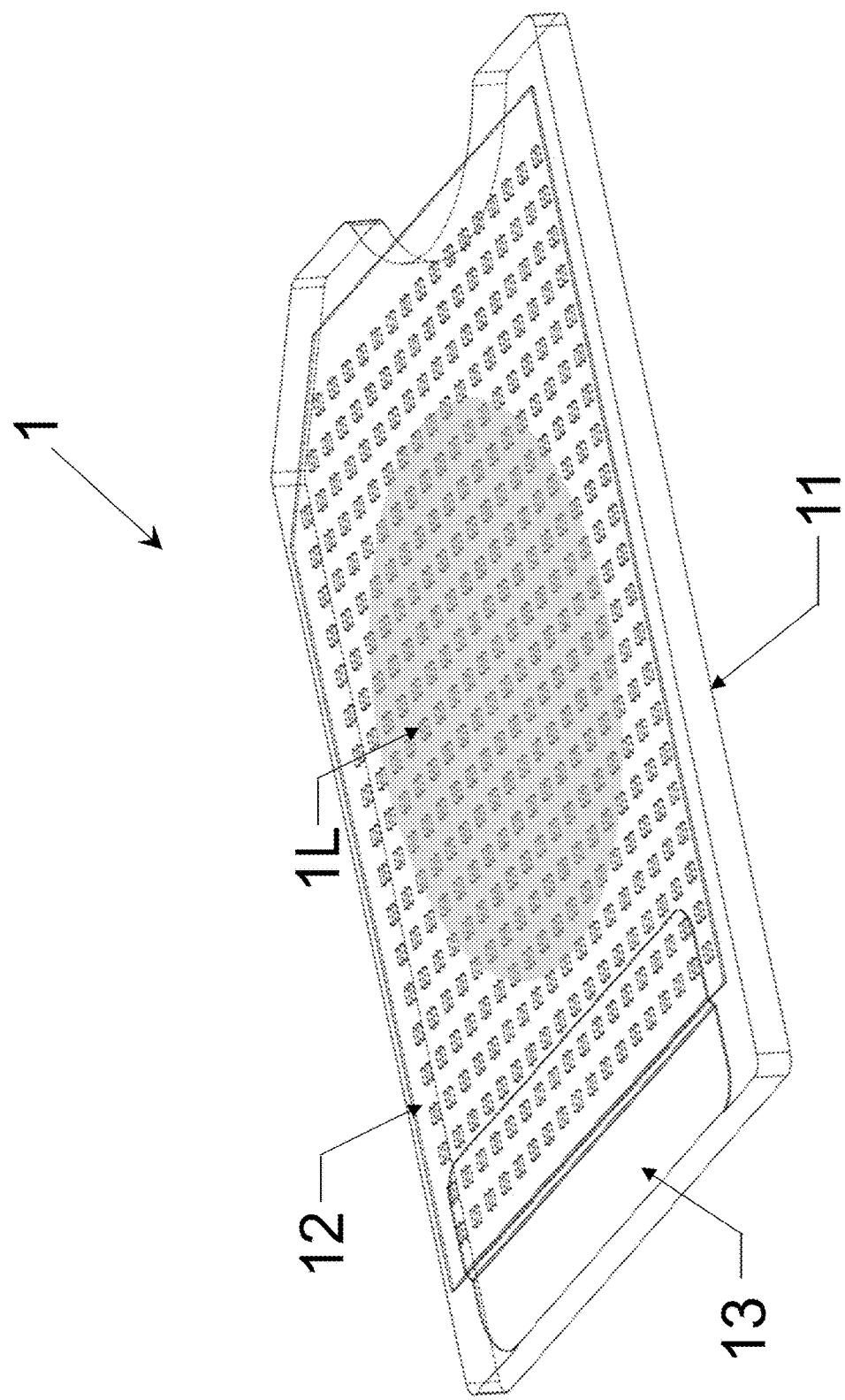
Fig. 1-F

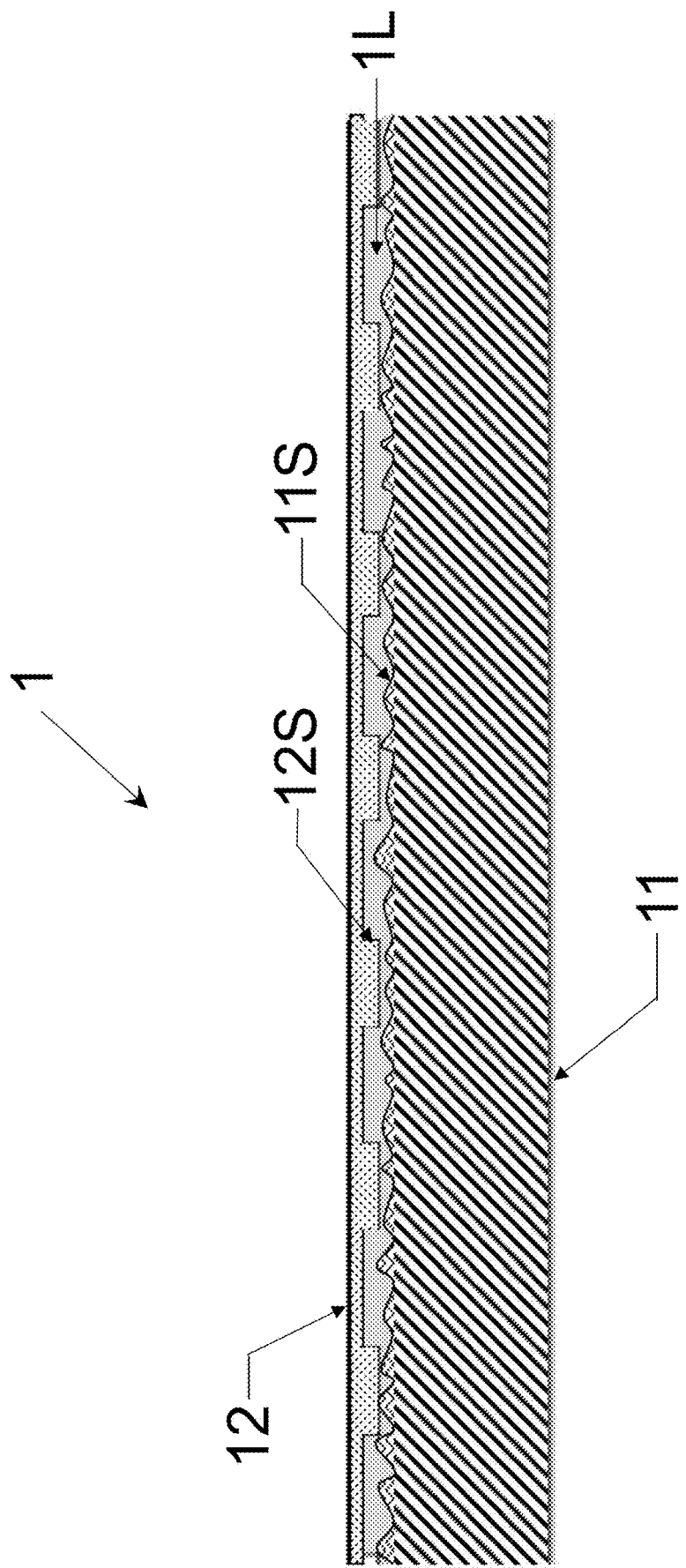
Fig. 1-G

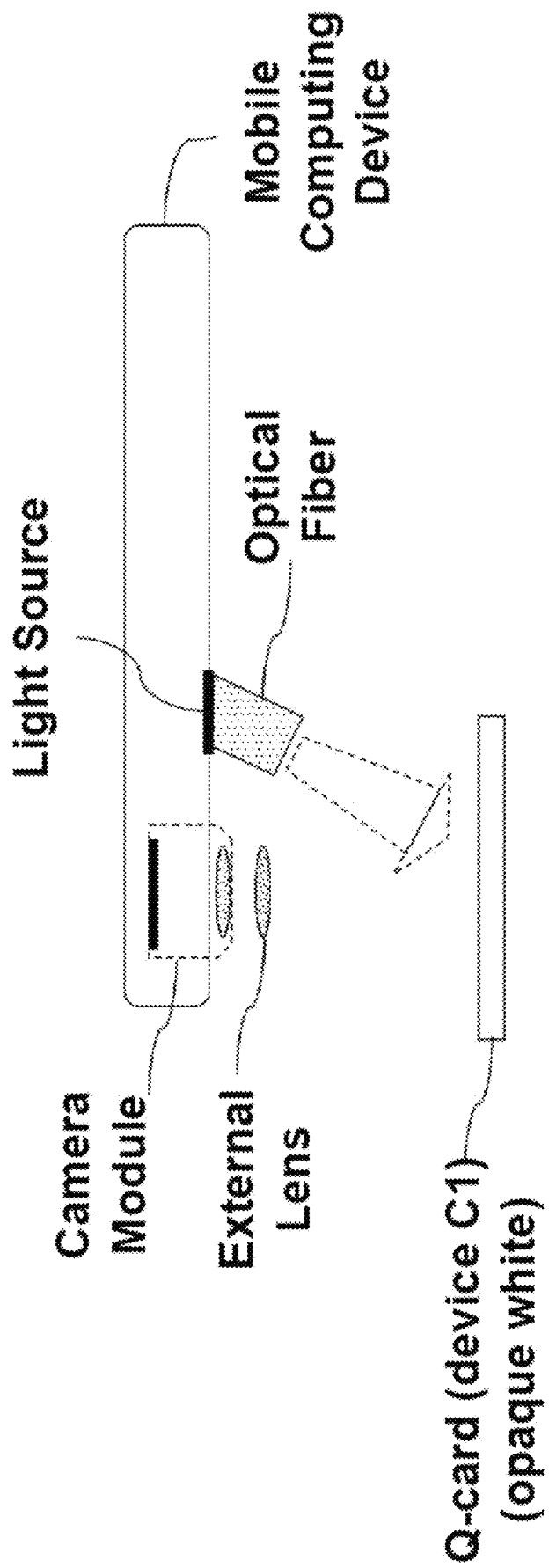
Fig. 2-A

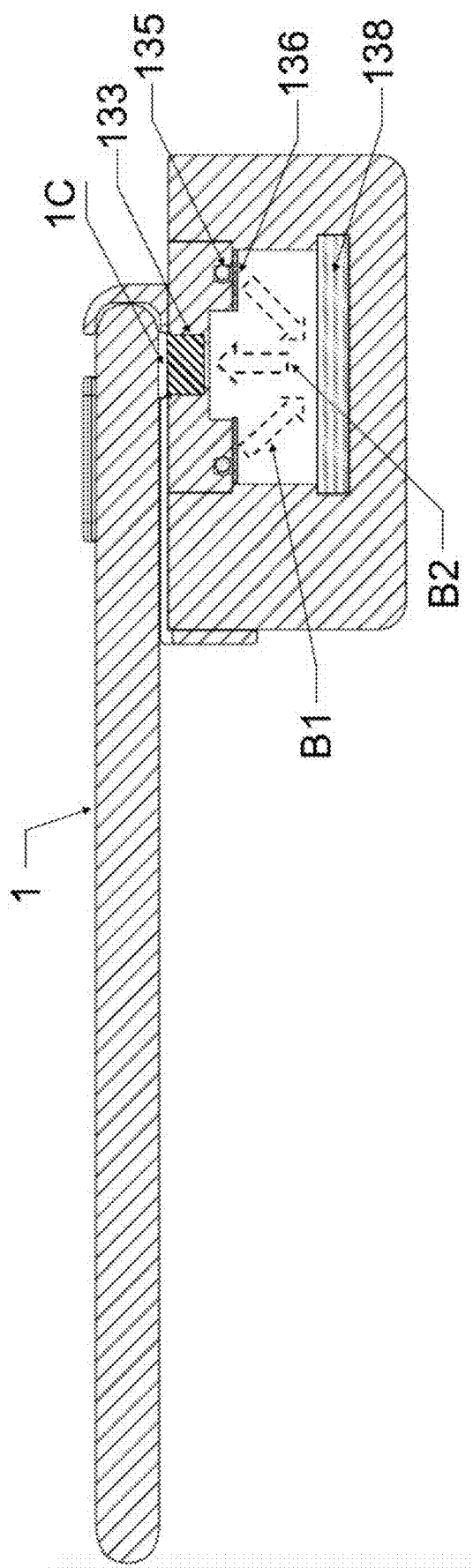
Fig. 2-B

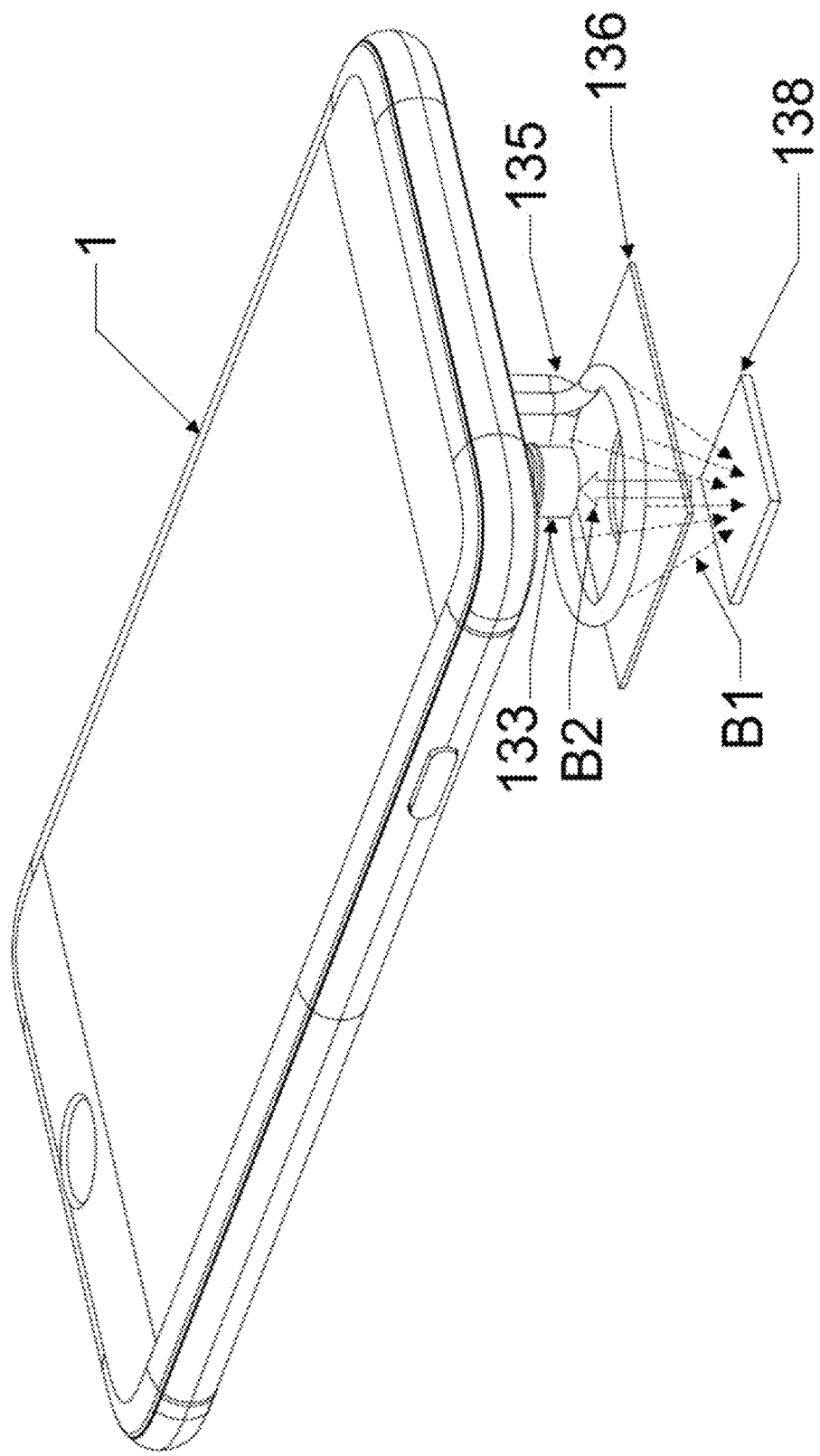
Fig. 2-C

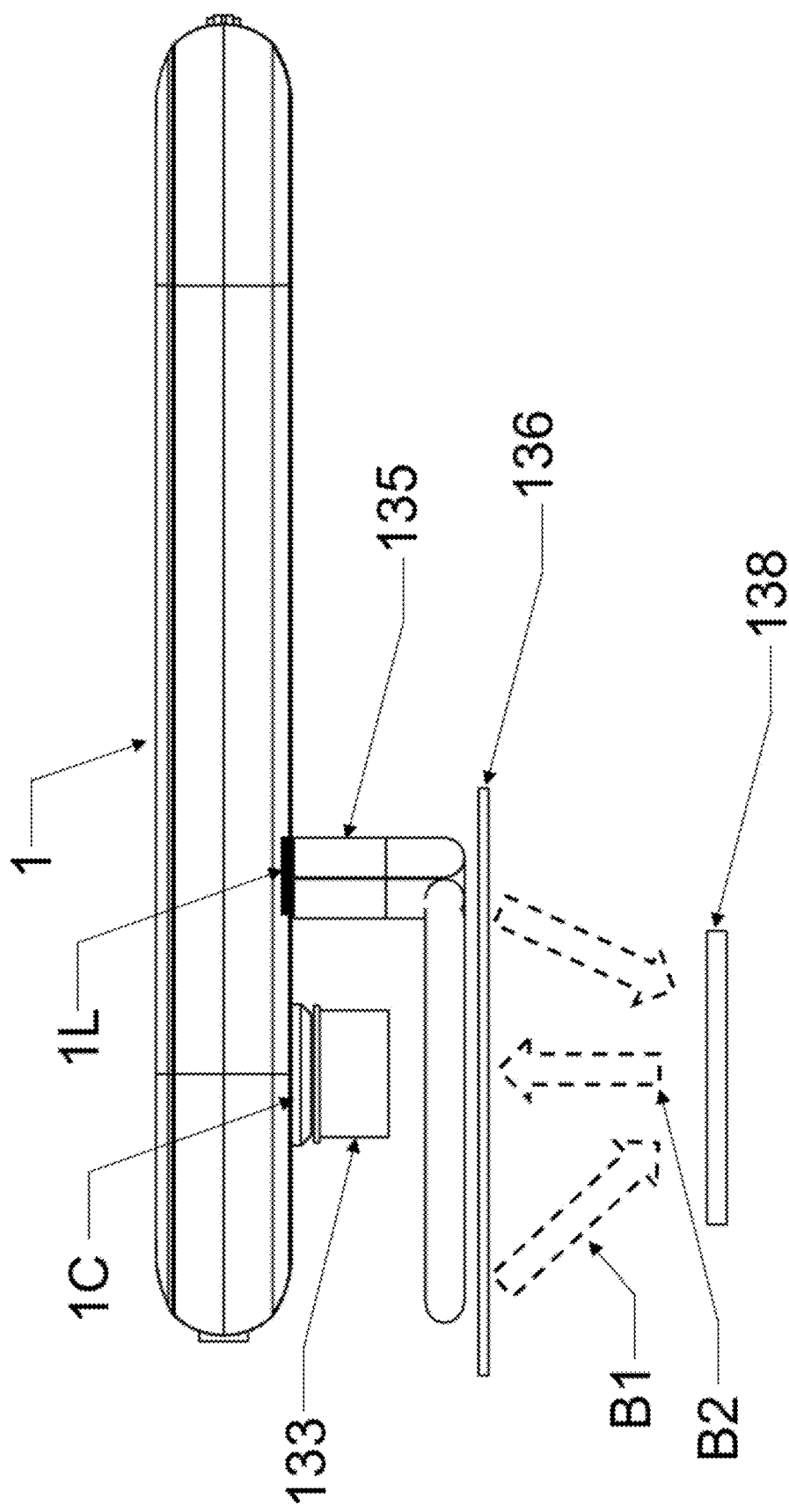
Fig. 2-D

ASSAY WITH TEXTURED SURFACE

CROSS-REFERENCE TO RELATED APPLICATIONS

This application is a continuation of U.S. patent Application Ser. No. 16/485,347, filed on Aug. 12, 2019, which is a § 371 national stage application of International Application PCT/US2018/018521 filed on Feb. 16, 2018, which claims the benefit of priority to U.S. Provisional Application ("U.S. Patent Application" hereafter) No. 62/460,088, filed on Feb. 16, 2017, U.S. Patent Application No. 62/460,091, filed on Feb. 16, 2017, U.S. Patent Application No. 62/460,083, filed on Feb. 16, 2017, U.S. Patent Application No. 62/460,076, filed on Feb. 16, 2017, U.S. Patent Application No. 62/460,075, filed on Feb. 16, 2017, U.S. Patent Application No. 62/460,069, filed on Feb. 16, 2017, U.S. Patent Application No. 62/460,062, filed on Feb. 16, 2017, U.S. Patent Application No. 62/460,047, filed on Feb. 16, 2017, U.S. Patent Application No. 62/459,972, filed on Feb. 16, 2017, U.S. Patent Application No. 62/459,920, filed on Feb. 16, 2017, PCT Application No. PCT/US18/18405, filed on Feb. 15, 2018, PCT Application No. PCT/US18/18108, filed on Feb. 14, 2018, PCT Application No. PCT/US18/18007, filed on Feb. 13, 2018, PCT Application No. PCT/US18/17716, filed on Feb. 9, 2018, PCT Application No. PCT/US18/17713, filed on Feb. 9, 2018, PCT Application No. PCT/US18/17712, filed on Feb. 9, 2018, PCT Application No. PCT/US18/17504, filed on Feb. 8, 2018. PCT Application No. PCT/US18/17501, filed on Feb. 8, 2018. PCT Application No. PCT/US18/17499, filed on Feb. 8, 2018. PCT Application No. PCT/US18/17489, filed on Feb. 8, 2018. PCT Application No. PCT/US18/17492, filed on Feb. 8, 2018. PCT Application No. PCT/US18/17494, filed on Feb. 8, 2018. PCT Application No. PCT/US18/17502, filed on Feb. 8, 2018, and PCT Application No. PCT/US18/17307, filed on Feb. 7, 2018, the contents of which are relied upon and incorporated herein by reference in their entirety. The entire disclosure of any publication or patent document mentioned herein is entirely incorporated by reference.

FIELD

Among other things, the present invention is related to devices and methods of performing biological and chemical assays, devices and methods of performing a biological and chemical using colorimetric approaches.

BACKGROUND

In bio/chemical assaying, there is a need to enhance light signal from a thin sample. For example, in colorimetric assay, when the sample thickness is very thin (e.g. 100 um (micron) or less), the color become very faint, become difficult to be observed, limiting the sensitivity of a colorimetric assay.

SUMMARY OF INVENTION

The following brief summary is not intended to include all features and aspects of the present invention. Among other thing, the present invention provides solutions to the to improve the sensitivity, speed, and easy-to-use of assaying by optical signal, such as colorimetric assays or fluorescent assays.

BRIEF DESCRIPTION OF THE DRAWINGS

The skilled artisan will understand that the drawings, described below, are for illustration purposes only. The drawings are not intended to limit the scope of the present teachings in any way. The drawings are not entirely in scale. In the figures that present experimental data points, the lines that connect the data points are for guiding a viewing of the data only and have no other means.

FIG. 1-A illustrates an example of opened assembled colorimetric assay sample card comprising a bottom plate, a top plate and an aluminum hinge, in accordance with an embodiment of the present invention.

FIG. 1-B and FIG. 1-C illustrate an example of bottom plate of the colorimetric assay sample card having textured microstructures on top surface, in accordance with an embodiment of the present invention.

FIG. 1-D and FIG. 1-E illustrate an example of top plate of the colorimetric assay sample card having pillar arrays of uniform heights on bottom surface, in accordance with an embodiment of the present invention.

FIG. 1-F and FIG. 1-G illustrates an example of ready-to-test colorimetric assay sample card comprising a bottom plate, a top plate, an aluminum hinge and sample liquid between top and bottom plates, in accordance with an embodiment of the present invention.

FIG. 2-A illustrates a test apparatus of colorimetric measurement of sample with textured surfaces using side illumination of a fiber.

FIG. 2-B, FIG. 2-C and FIG. 2-D illustrates a test apparatus of colorimetric measurement of sample with textured surfaces using ring illumination of a fiber.

DETAILED DESCRIPTION OF EXEMPLARY EMBODIMENTS

Figure 3:
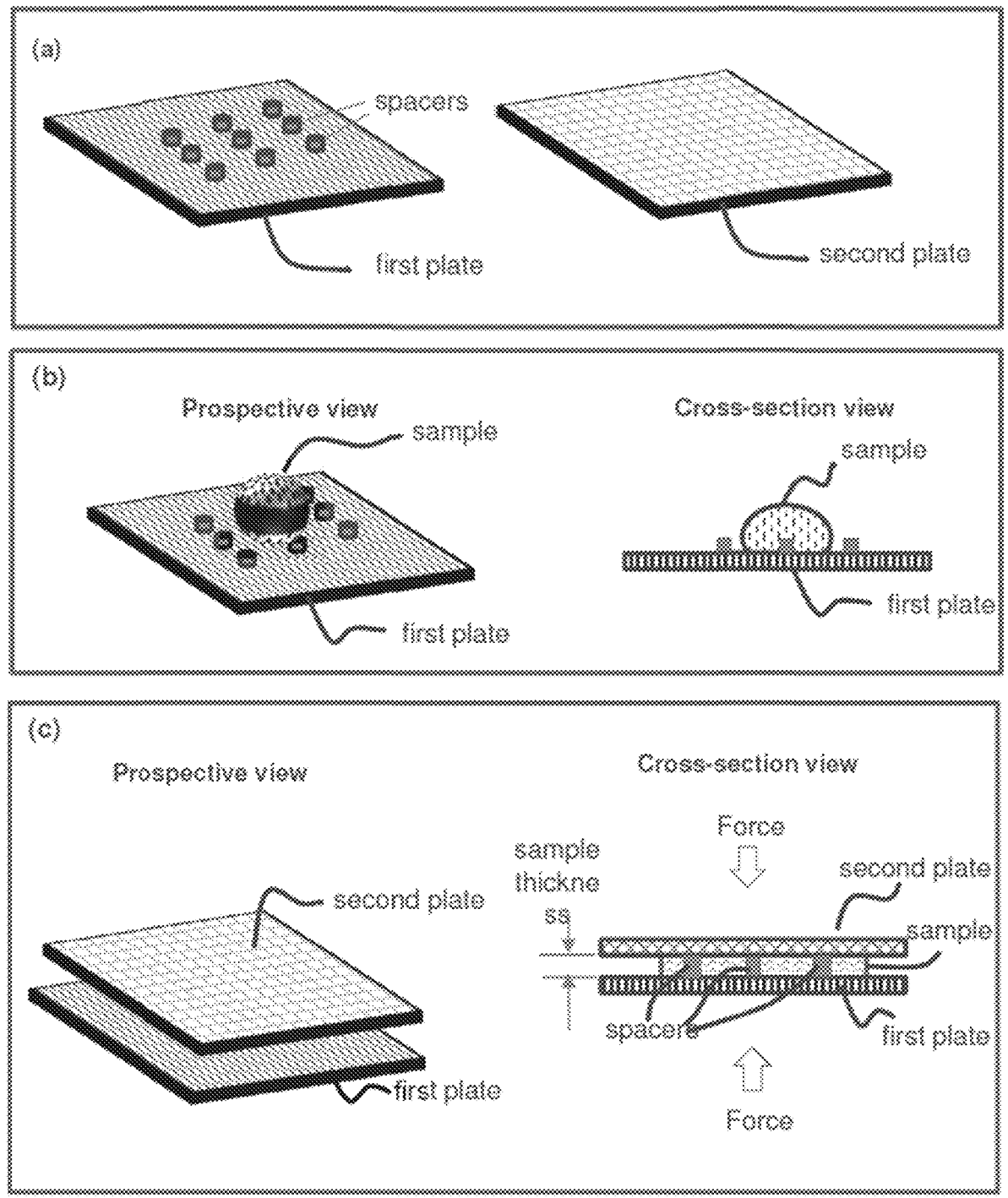
FIG. 3 is an illustration of a CROF (Compressed Regulated Open Flow) embodiment. Panel (a) illustrates a first plate and a second plate wherein the first plate has spacers. Panel (b) illustrates depositing a sample on the first plate (shown), or the second plate (not shown), or both (not shown) at an open configuration. Panel (c) illustrates (i) u sing the two plates to spread the sample (the sample flow between the plates) and reduce the sample thickness, and (ii) using the spacers and the plate to regulate the sample thickness at the closed configuration. The inner surface of each plate may have one or a plurality of binding sites and or storage sites (not shown).
Figure 4:
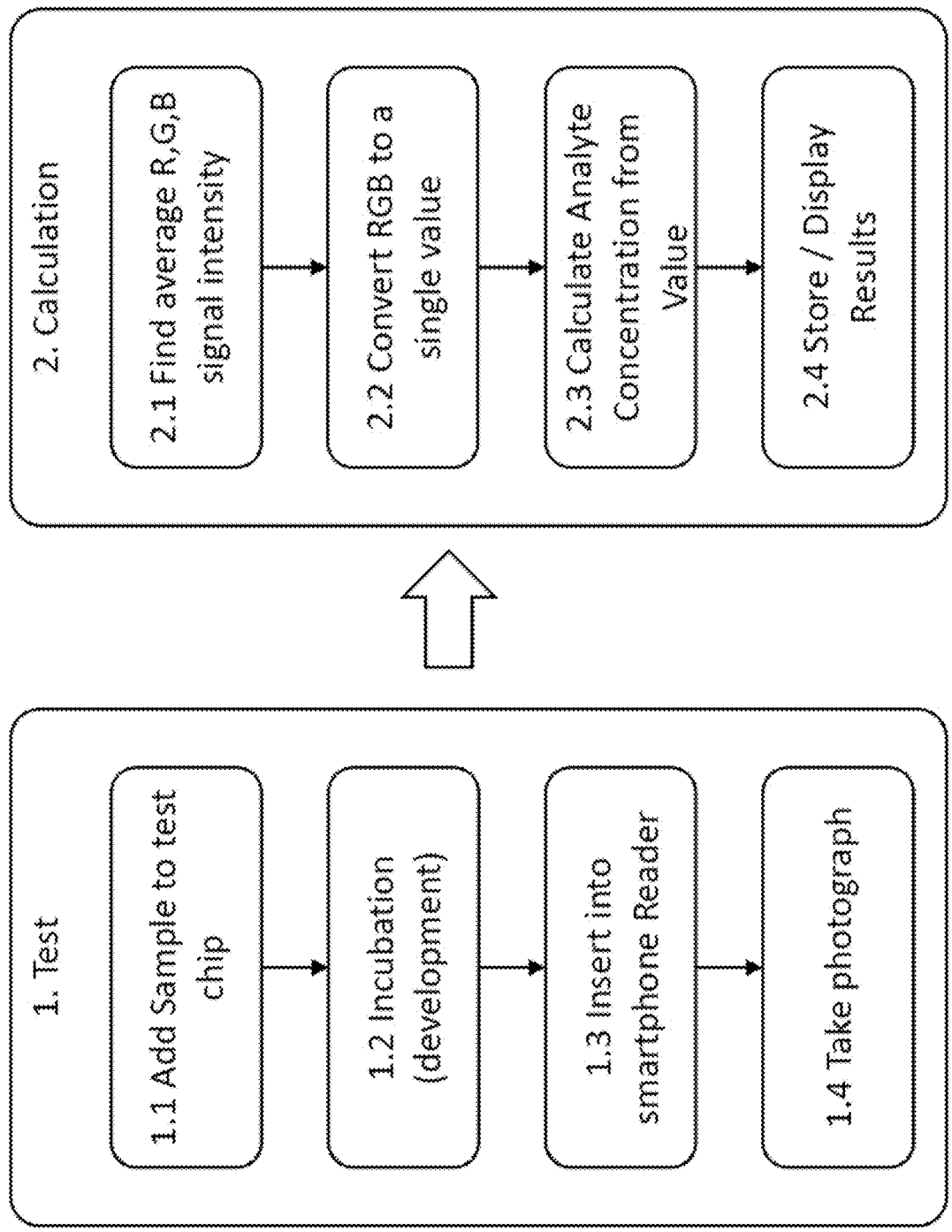
FIG. 4 A diagram of a process of testing heavy metal in water.

The following detailed description illustrates some embodiments of the invention by way of example and not by way of limitation. The section headings and any subtitles used herein are for organizational purposes only and are not to be construed as limiting the subject matter described in any way. The contents under a section heading and/or subtitle are not limited to the section heading and/or subtitle, but apply to the entire description of the present invention.

The citation of any publication is for its disclosure prior to the filing date and should not be construed as an admission that the present claims are not entitled to antedate such publication by virtue of prior invention. Further, the dates of publication provided can be different from the actual publication dates which can need to be independently confirmed.

A. QMAX Colorimetric Assay with Textures Reflective Scattering Surfaces

In an assay involving a detection of light signal, such as colorimetric assay or fluorescese assay, a small container to hold a liquid sample and passes a light beam though the sample to measure the light or the color of the sample. When the sample is very thin, the light or color becomes faint and difficult measure.

The present invention provides, among other thing, solution to get a stronger optical signal in a thin sample.

One novelty of the present invention is to use QMAX card (that has two movable plates) to make a sample into a very uniform thin layer (less than 200 um).

Another novelty of the present invention is to use a textured reflective surface on a surface of one of the two plates to enhance an optical signal, particularly for colorimetric assay and/or fluorescence assay.

In the present invention, we observed that the color signal of a colorimetric assay can be significantly increased by using a reflective textured surface as one of the wall of the chamber can significantly increase the color signal.

According the present invention, a device uses to plates to sandwich a sample into a thin layer, wherein one of the plate is transparent and the other plate has a textured reflective surface on its sample contact area. The probing light enters the sample from the transparent plate, goes through the sample, and diffusively reflected by the textured surface back to the transparent plate. We have observed that such arrangement can significantly increase the color signal even the sample as thin as 30 um or less.

Furthermore, according to the present invention, the device further comprise a dry reagent coated on one of the plate, so that a liquid sample can dropped on one or both of the plate, close the plates, and then measurement. The sample thickness can be 150 um or less, making the dry regent mixed with the sample in a short time, to speed up the total measurement time.

The terms "CROF Card (or card)", "COF Card", "QMAX-Card", "Q-Card", "CROF device", "COF device", "QMAX-device", "CROF plates", "COF plates", and "QMAX-plates" are interchangeable, except that in some embodiments, the COF card does not comprise spacers; and the terms refer to a device that comprises a first plate and a second plate that are movable relative to each other into different configurations (including an open configuration and a closed configuration), and that comprises spacers (except some embodiments of the COF) that regulate the spacing between the plates. The term "X-plate" refers to one of the two plates in a CROF card, wherein the spacers are fixed to this plate. More descriptions of the COF Card, CROF Card, and X-plate are described in in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

Device_0 (General)

N1. In some embodiments, according to the present invention, a device for assaying a sample using optical signal, comprising:

a first plate, a second plate, spacers, and a textured surface, wherein:
  i. the first and second plates are movable relative to each other into different configurations;
  ii. one or both plates are flexible;
  iii. the second plate has, on its inner surface, have textured structures for scattering the light illuminated on the surface;
  iv. the textured surface can be, but is not limited to a bumpy, wavy roughly surface;
  v. the textured surface is periodic or aperiodic;
  vi. the textured surface's average roughness range is preferred to be, but is not limited to 2 um-5 um;
  vii. the spacers are fixed to the inner surface of the first plate and have a predetermined uniform height;
  viii. the preferred height of spacers is larger than the average roughness of the textured surface and smaller than 100 um;

wherein on of the configuration is an open configuration, in which: two plates are partially or entirely separated apart, the spacing between the plates is not regulated by the spacers, and the sample is deposited on one or both of the plates;

wherein on of the configuration is a closed configuration, which is configured after the sample deposition in the open configuration, and in the closed configuration: at least part of the deposited sample is compressed by the two plates into a continuous layer; wherein the sample is in liquid form.

Device_C1 (for Colorimetric Signal)

A sample handling device for enhancing optical signal (Q-card), comprising:

A first plate, a second plate, spacers and textured surface, wherein:
  i. the plates are movable relative to each other into different configurations;
  ii. one or both plates are flexible;
  iii. the second plate has, on its inner surface, have textured structures for scattering the light illuminated on the surface;
  iv. the textured surface can be, but is not limited to a bumpy, wavy roughly surface;
  v. the textured surface can be periodic or aperiodic;
  vi. the textured surface's average roughness range is preferred to be, but is not limited to 2 um-5 um;
  vii. the spacers are fixed to the inner surface of the first plate and have a predetermined uniform height;
  viii. the preferred height of spacers is larger than the average roughness of the textured surface and smaller than 100 um;

wherein on of the configuration is an open configuration, in which: two plates are partially or entirely separated apart, the spacing between the plates is not regulated by the spacers, and the sample is deposited on one or both of the plates;

wherein on of the configuration is a closed configuration, which is configured after the sample deposition in the open configuration, and in the closed configuration: at least part of the deposited sample is compressed by the two plates into a continuous layer; wherein the sample is in liquid form.

In some embodiments, the textured surface is made of opaque white material.

Device_C2 (for Colorimetric Signal)

A sample handling device for enhancing optical signal (Q-card), comprising:

A first plate, a second plate, spacers and textured surface, wherein:
  i. the plates are movable relative to each other into different configurations;
  ii. one or both plates are flexible;
  iii. the second plate has, on its inner surface, have textured structures for scattering the light illuminated on the surface;
  iv. the textured surface can be, but is not limited to a bumpy, wavy roughly surface;
  v. the textured surface can be periodic or aperiodic;

vi. the textured surface's average roughness range is preferred to be, but is not limited to 2 um-5 um;
vii. the spacers are fixed to the inner surface of the first plate and have a predetermined uniform height;
viii. the preferred height of spacers is larger than the average roughness of the textured surface and smaller than 100 um;

wherein on of the configuration is an open configuration, in which: two plates are partially or entirely separated apart, the spacing between the plates is not regulated by the spacers, and the sample is deposited on one or both of the plates;

wherein on of the configuration is a closed configuration, which is configured after the sample deposition in the open configuration, and in the closed configuration: at least part of the deposited sample is compressed by the two plates into a continuous layer; wherein the sample is liquid form.

In some embodiments, the textured surface is made of semi-opaque white material, and the transmissivity is 10%~30%.

Device_F (for Fluorescent Signal)

A sample handling device for enhancing optical signal (Q-card), comprising:

A first plate, a second plate, spacers and textured surface, wherein:
i. the plates are movable relative to each other into different configurations;
ii. one or both plates are flexible;
iii. the second plate has, on its inner surface, have textured structures for scattering the light illuminated on the surface;
iv. the textured surface can be, but is not limited to a bumpy, wavy roughly surface;
v. the textured surface can be periodic or aperiodic;
vi. the textured surface's average roughness range is preferred to be, but is not limited to 2 um-5 um;
vii. the spacers are fixed to the inner surface of the first plate and have a predetermined uniform height;
viii. the preferred height of spacers is larger than the average roughness of the textured surface and smaller than 100 um;

wherein on of the configuration is an open configuration, in which: two plates are partially or entirely separated apart, the spacing between the plates is not regulated by the spacers, and the sample is deposited on one or both of the plates;

wherein on of the configuration is a closed configuration, which is configured after the sample deposition in the open configuration, and in the closed configuration: at least part of the deposited sample is compressed by the two plates into a continuous layer;

wherein the sample is in liquid form.

In some embodiments, the textured surface is made of opaque white material or coated with reflective metal film, the metal film can be, but is not limited to aluminum, silver and gold. The preferred thickness range of the metal film is preferred to be, but not limited to be 10 nm~100 nm.

Apparatus (for Colorimetric Signal).A1

A testing apparatus, comprising:
a) a sample handling device for enhancing optical signal (Device_C1), according to the above device claim;
b) a mobile computing device having a camera module and a light source;
c) an Illumination optics, comprising a tilted optical fiber;
d) an external lens;

wherein the light source emits white light;

wherein the light source and camera module are on the same face of the mobile computing device;

wherein the Q-card is put right under camera module, the preferred distance between them is 15 mm-20 mm;

wherein the external lens is put between the Q-card and camera module so that the sample in Q-card is in the working distance of camera module, and the preferred focal length of external lens is 12~18 mm, and the distance between lens and camera module is preferred to be as small as possible and no larger than 3 mm;

wherein the optical fiber guide the light emitted from the light source to illuminate on the sample area right under the camera module;

wherein one end face of the optical fiber is put under the aperture of the light source, and the distance between them is preferred to be as small as possible and no larger than 3 mm;

wherein the diameter of the optical fiber is configured to be equal to the diameter of the light source aperture;

wherein the tilt angle in which the optical fiber is mounted is set to make the center light beam emitted out from the fiber illuminate on the sample area right under the camera module.

Apparatus (for Colorimetric Signal).A2

A testing apparatus, comprising:
a) a sample handling device for enhancing optical signal (Device_C2), according to the above device claim;
b) a mobile computing device having a camera module and a light source;
c) an Illumination optics, comprising a pair of reflective mirrors;
d) an external lens;

wherein the light source emits white light;

wherein the light source and camera module are on the same face of the mobile computing device;

wherein the Q-card is put right under camera module, the preferred distance between them is 5~10 mm;

wherein the external lens is put between the Q-card and camera module so that the sample in Q-card is in the working distance of camera module, and the preferred focal length of external lens is 4~8 mm, and the preferred distance between lens and camera module is preferred to be as small as possible and no larger than 3 mm;

wherein the illumination optics turns the light emitted from the light source to back-illuminate the sample on Q-card, and each mirror turns the light by 90 degree;

wherein the mirrors are mounted under the Q-card, and one mirror is in a line with the light source, and another one is in a line with the camera module, and the preferred distance between the Q-card and mirrors is 5 mm-10 mm.

Apparatus (for Colorimetric Signal).A3

A testing apparatus, comprising:
a) a sample handling device for enhancing optical signal (DeviceS2), according to the above device claim;
b) a mobile computing device having a camera module;
c) a separate light source;
d) an external lens;

wherein the light source emits white light, and the light source is put under the Q-card and in a line with the camera module, and the preferred distance between the light source and Q-card is 5 mm-10 mm.

wherein the Q-card is put right under camera module, the preferred distance between them is 5~10 mm;

wherein the external lens is put between the Q-card and camera module so that the sample in Q-card is in the working distance of camera module, and the preferred focal length of external lens is 4~8 mm, and the preferred distance between lens and camera module is preferred to be as small as possible and no larger than 3 mm;

Optical Signals

According the present invention, the optical signal that can by enhanced by the textured surfaces of the device of any prior embodiment, is selected from a group of colors in the sample, fluorescence, luminescence (electrical, chemical, photo, or electrical-chemical), and/or other light from emitters.

Apparatus for Fluorescent Signal).A4

A testing apparatus, comprising:
  a) a sample handling device for enhancing optical signal (Device_F), according to the above device claim;
  b) a mobile computing device having a camera module;
  c) a separate light source;
  d) an Illumination optics, comprising tilted reflective mirror;
  e) filters, comprising a long pass filter and a short pass filter;
  f) an external lens;
  wherein the light source is a laser diode;
  wherein the tilt mirror turns the light emitted from the light source to illuminate on the sample area right under the camera module;
  wherein the light illuminates on the sample in an oblique angle, preferred angle is >60 degree;
  wherein the Q-card is put right under camera module, the preferred distance between them is 15 mm-20 mm;
  wherein the external lens is put between the Q-card and camera module so that the sample in Q-card is in the working distance of camera module, and the preferred focal length of external lens is 12 mm-18 mm, and the preferred distance between lens and camera module is preferred to be as small as possible and no larger than 3 mm;
  wherein the short pass filter is put in front of the aperture of the light source;
  wherein the long pass filter is put between the external lens and camera module.

Method

A method for analyzing the optical signal of sample, comprising the steps of:
  a) collecting a sample liquid;
  b) obtaining a device of any prior embodiment;
  c) depositing the sample on one or both of the plates of the device when the plates are in an open configuration;
  d) bringing the two plates together and pressing the plates into the closed configuration so that the sample forms a liquid layer between the two plates;
  e) inserting the device into the testing apparatus;
  f) turning on the light source of the testing apparatus;
  g) using camera module capture an image of the sample; and
  h) the mobile computing device process the image to analyze colorimetric or fluorescent signal of the image to get some property of the sample.

Application

The Q-card device, testing apparatus and the method above can be applied to detect presence and level of the analyte of interest in the following fields:
  1) Food science and safety: testing pH, ammonia, nitrite, nitrate, heavy metal, bacteria level, etc. in drinking water; testing bacteria, lactose, additive, particular protein level, etc. in milk;
  2) Personal health monitoring: glucose, alcohol, etc. in saliva, urine and breath.
  3)

In some embodiments, a device for enhancing an optical signal in assaying comprises:
  a first plate, a second plate, spacers, and a light scattering layer, wherein:
    i. the first and second plates are movable relative to each other into different configurations, and have, on its respective inner surface, a sample contact area for contacting a sample that contains an analyte;
    ii. one or both of the plates are flexible;
    iii. the first plate is transparent to the light, and
    iv. the second plate substantially reflect light and comprises an inner surface a light scattering layer that has a rough topology;
  wherein one of the configurations is an open configuration, in which the average spacing between the inner surfaces of the two plates is at least 200 um, and the sample is deposited on one or both of the plates;
  wherein another of the configurations is a close configuration, which is configured after the sample deposition in the open configuration, and in the closed configuration: at least part of the sample is between the two plates and the average spacing between the inner surfaces of the plates is less than 200 um; and
  wherein in the closed configuration, the light scattering layer enhances trapping a probe light between the inner surface of the two plates.

In some embodiments, in the device, the light scattering surface of the second plate comprises:
  i. the textured surface can be, but is not limited to a bumpy, wavy roughly surface;
  ii. the textured surface can be periodic or aperiodic;
  iii. the textured surface's average roughness range is preferred to be, but is not limited to 2 um-5 um; or
  iv. the spacers are fixed to the inner surface of the first plate and have a predetermined uniform height; and
  v. a combination of thereof.

C1. The device or system of any prior embodiments, wherein the light scattering layer can be made of highly reflectively opaque white material with reflectivity at least 50%, 60%, 70%, 80%, 90%, 100%, or in a range between any of the two values.

C2. The device or system of any prior embodiments, wherein the reflection spectrum of the light scattering surface is within the range of 300 nm to 1000 nm.

C3. The device or system of any prior embodiments, wherein the light scattering layer can be made of semi-opaque white material, and the transmissivity is 10%~30%.

C4. The device or system of any prior embodiments, wherein the light scattering layer can be made of reflective metal film, wherein the light scattering layer can be made of opaque white dielectric film.

C5. The device or system of any prior embodiments, wherein the the light scattering layer has textured surfaces with $R_a$ (arithmetic average roughness) of 0.5 um-200 um, $R_{sm}$ (mean spacing of the asperities) of >0.5 um and $R\Delta_a$ (average slop of the profile) >0.1

C6. The device or system of any prior embodiments, wherein the textured surface can be periodic or aperiodic, wherein the shape of a single feature on the textured surface can be but not limited to square, triangle, sharp corner.

C7. The device or system of any prior embodiments, wherein the height of spacers is larger than the average roughness of the textured surface and smaller than 200 um.

The device or system of any prior embodiments, the average roughness height ($R_a$) of the textured reflective need to be at least 20% of the wavelength of the illumination light and can be up to 5-fold of the spacing between the first plate and second plate, or in range between these two values;

The device or system of any prior embodiments, the average lateral feature size ($b_a$) need to be at least 20% and up to 10-fold of the wavelength of the illumination light, or in range between these two values;

The device or system of any prior embodiments, the average period ($b_a$) need to be at least 50% and up to 1000-fold of the wavelength of the illumination light, or in range between these two value.

FIG. 1-A is the schematic illustration of colorimetric assay sample card 1 in open status. Sample card 1 comprises a top plate 12, a bottom plate 11 and an aluminum hinge 13. Hinge 13 attach top plate 12 to bottom plate 13.

The height of the random scattering structures is from 1 nm to 200 nm, from 1 nm to 300 nm, and from 1 nm to 5000 nm.

In some embodiments, the reflection surface can be done by random nanoparticles of the same size or different size.

In some embodiments, the reflective range from 50% to 100%, from 30% to 100% and from 50% to 80%. They are either wide band or narrow band in spectrum, FIG. 1-B and FIG. 1-C are the schematic illustrations of bottom plate 11 in sample card 1, shown from isometric view and cross-section view respectively. The material for the bottom plate 11 is nonabsorbent and has opaque white color. It can be, but is not limited to, white polyethylene. The bottom plate 11 has textured surface 11S on one of its top surface (i.e. the surface facing the top plate 12). The textured surface 11S can be random microstructures or periodic microstructures. For random microstructures, it can be, but is not limited to, a bumpy, wavy or rough surface. In one embodiment, the textured surface is the bumpy surface of the matte finish of the white polystyrene sheet with average roughness of 2~3 um. For periodic microstructures, it can be, but is not limited to round, rectangular and triangular pillars protruding from a surface of the bottom plate with a square, hexagonal or other lattices. A notch 11N is fabricated on one side of bottom plate 11 to make it easy to open top plate 12. A triangle gap 11C is fabricated at one corner of bottom plate 11 to easily differentiate the front and bottom surface of bottom plate 11.

FIG. 1-D and FIG. 1-E are the schematic illustrations of top plate 12 in sample card 1, shown from isometric view and cross-section view respectively. The material for the top plate is transparent and can be, but is not limited to, PMMA. On bottom surface of the top plate (i.e. the surface facing the bottom plate 11), there are periodic micro-size pillar arrays 12S with uniform heights. The pillar array can be, but is not limited to, rectangular pillars with square lattice. In one embodiment, the top plate is made of PMMA of 175 um thickness and the pillar array has a square lattice with the period of 120 um*110 um. And each pillar has the rectangular shape with the dimension of 30 um*40 um and the pillar height is 30 um. A triangle gap 12C is fabricated at one corner of bottom plate 12 to easily differentiate the front and bottom surfaces of top plate 12.

FIG. 1-F and FIG. 1-G are the schematic illustrations of colorimetric assay sample card 1 in closed status with sample liquid, shown from isometric view and cross-section view respectively. The sample liquid 1L is embedded between top plate 12 and bottom plate 11. The textured surface 11S of bottom plate 11 is towards the bottom surface of the top plate 12 with pillar array 12S. The average liquid layer thickness of the sample liquid 1L is uniform and determined by height of the pillar array 12S on top plate 12. Hence, the volume of the sample liquid 1L holding in sample card 1 per unit area in this present invention can be accurately determined. Under the illumination of white light, textured surface 11S of bottom plate 11 helps deflect the light beams to increase the light path inside the sample liquid layer 1L. Hence, light absorption by the colored compounds in sample liquid 1L is increased and the color change is enhanced.

FIGS. 2-A, 2-B and 2-C are the schematic views showing details of system 10 reading a colorimetric card, and particularly of device 13. FIG. 15-A is the sectional view showing details of device 13. And FIG. 15-B and FIG. 15-C are the schematic views only showing the configuration of the optics elements in device 13. These figures illustrate the functionality of the elements that were described above with reference to FIG. 14. The light emitted from light source 1L is coupled into side-emitting optical fiber ring 135 from the two end faces of fiber ring 135 and travels inside along the ring. Beam B1 is emitted out from the side wall of fiber ring and go through the diffuser film 136. Beam B1 illuminates the sample area of colorimetric sample card 138 right under the camera 1C from front side to create uniform illumination. The illuminated sample area absorbs part of beam B1 and reflects the beam B1 to beam B2. Beam B2 is collected by lens 133 and gets into camera 1C Lens 133 creates an image of the sample area on the image sensor plane of camera 1C. Smartphone 1 captures and processes the image to analyze the color information in the image to quantify the color change of the colorimetric assay.

In some embodiments, no spacers are used in regulating the sample thickness between the two plates.

In some embodiments, the textured reflective surface of the plate has one or a combination of each of the parameters:
Optical Signal Enhanced by Textured Surfaces Colorimetric assay's signal can be enhanced by the textured surfaces. In colorimetric assay, under the illumination of white light, a specific wavelength of light is absorbed by the colored compounds, which results in the color change. Hence, to get stronger color change signal, more light of the specific absorbing wavelength of the color compounds needs to get absorbed. And based on Beer-Lambert law which determines how much percent of light is absorbed when light passing through a light absorbing medium, the way to increase the light absorption in a colorimetric assay is to increase the light path in the sample liquid. Compared to a flat reflective surface, the textured surface can make the small-angle incident light be reflected to a large-angle emergent light by scattering to increase the light path in the sample liquid. And textured surface can scatter the incident light several times in the sample liquid to increase the light path before the light emits out.

Fluorescent signal of an assay can also be enhanced by the textured surface. In fluorescent assay, under the illumination of excitation light with a specific wavelength, the emitting fluorescent intensity is proportional to the product of fluorescent dye's quantum yield and absorbed amount of excitation light. The textured surface increases the light path of excitation light in the sample liquid by scattering hence more excitation light is absorbed by the fluorescent molecules.

A test apparatus comprises the device, a light source, an optical fiber and an imager wherein the light source emits light within wavelength range of 300 nm to 1000 nm;

wherein the light source and imager are on a same plane;

wherein the Q-card is put right under the imager, the preferred distance between them is 15 mm-20 mm;

wherein the optical fiber guide the light emitted from the light source to illuminate on the sample area right under the camera module;

wherein one end face of the optical fiber is put under the aperture of the light source, and the distance between them is preferred to be as small as possible and no larger than 10 mm;

wherein the diameter of the optical fiber is configured to be equal to the diameter of the light source aperture;

wherein the tilt angle in which the optical fiber is mounted is set to make the center light beam emitted out from the fiber illuminate on the sample area right under the camera module.

A test apparatus comprises the device, a light source, a ring-shape optical fiber and an image, wherein the light source emits light within wavelength range of 300 nm to 1000 nm;

wherein the ring fiber is a side-emitting optical fiber that can outcouple light from the wall of the fiber;

wherein the ring fiber is in a circle around the imager;

wherein the Q-card is put right under the imager, the preferred distance between them is 15 mm-20 mm;

wherein the light emits from the side of the ring-shape fiber to illuminate the sample;

wherein both end faces of the ring-shape optical fiber are put under the aperture of the light source;

wherein a light diffuser is put between the ring-shape fiber and sample to diffuse the light emitting from the ring fiber;

B. Spacers, Hinges, and Opening Notch

In biological and chemical assaying (i.e. testing), a device and/or a method that simplifies assaying operation or accelerates assaying speed is often of great value.

In the QMAX (Q: quantification; M: magnifying; A: adding reagents; X: acceleration; also known as compressed regulated open flow (CROF)) assay platform, a QMAX card uses two plates to manipulate the shape of a sample into a thin layer (e.g. by compressing) (as illustrated in FIG. 1). In certain embodiments, the plate manipulation needs to change the relative position (termed: plate configuration) of the two plates several times by human hands or other external forces. There is a need to design the QMAX card to make the hand operation easy and fast.

In QMAX assays, one of the plate configurations is an open configuration, wherein the two plates are completely or partially separated (the spacing between the plates is not controlled by spacers) and a sample can be deposited. Another configuration is a closed configuration, wherein at least part of the sample deposited in the open configuration is compressed by the two plates into a layer of highly uniform thickness, the uniform thickness of the layer is confined by the inner surfaces of the plates and is regulated by the plates and the spacers.

In a QMAX assay operation, an operator often needs to add assay reagents into the sample in a controlled fashion. For instance, in some embodiments, the reagents (e.g. detection agent and binding agent) are coated on the plate surface of the QMAX device, and some reagents (e.g. detection agent) are released into the sample at an appropriate timing during the assay process. Among many others, in some cases, it is desirable for the detection agent to be added after the substantial binding of the target analyte by the binding agent. In other cases, it is desirable to add the detection agent after the formation of the thin film of the sample. In other cases, it is desirable to delay the addition of the detection agent by a specified time period. The present invention is to provide devices and methods for achieving these goals as well as for making bio/chemical sensing (including, not limited to, immunoassay, nucleic assay, electrolyte analysis, etc.) faster, more sensitive, less steps, easy to perform, smaller amount of samples required, less or reduced (or no) needs for professional assistance, and/or lower cost, than many current sensing methods and devices.

The term "compressed open flow (COF)" refers to a method that changes the shape of a flowable sample deposited on a plate by (i) placing other plate on top of at least a part of the sample and (ii) then compressing the sample between the two plates by pushing the two plates towards each other; wherein the compression reduces a thickness of at least a part of the sample and makes the sample flow into open spaces between the plates. The term "compressed regulated open flow" or "CROF" (or "self-calibrated compressed open flow" or "SCOF" or "SCCOF") (also known as QMAX) refers to a particular type of COF, wherein the final thickness of a part or entire sample after the compression is "regulated" by spacers, wherein the spacers are placed between the two plates. Here the CROF device is used interchangeably with the QMAX device.

The term "spacers" or "stoppers" refers to, unless stated otherwise, the mechanical objects that set, when being placed between two plates, a limit on the minimum spacing between the two plates that can be reached when compressing the two plates together. Namely, in the compressing, the spacers will stop the relative movement of the two plates to prevent the plate spacing becoming less than a preset (i.e. predetermined) value.

The term "a spacer has a predetermined height" and "spacers have a predetermined inter-spacer distance" means, respectively, that the value of the spacer height and the inter spacer distance is known prior to a QMAX process. It is not predetermined, if the value of the spacer height and the inter-spacer distance is not known prior to a QMAX process. For example, in the case that beads are sprayed on a plate as spacers, where beads are landed at random locations of the plate, the inter-spacer distance is not predetermined. Another example of not predetermined inter spacer distance is that the spacers moves during a QMAX processes.

The term "a spacer is fixed on its respective plate" in a QMAX process means that the spacer is attached to a location of a plate and the attachment to that location is maintained during a QMAX (i.e. the location of the spacer on respective plate does not change) process. An example of "a spacer is fixed with its respective plate" is that a spacer is monolithically made of one piece of material of the plate, and the location of the spacer relative to the plate surface does not change during the QMAX process. An example of "a spacer is not fixed with its respective plate" is that a spacer is glued to a plate by an adhesive, but during a use of the plate, during the QMAX process, the adhesive cannot hold the spacer at its original location on the plate surface and the spacer moves away from its original location on the plate surface.

The term "open configuration" of the two plates in a QMAX process means a configuration in which the two plates are either partially or completely separated apart and the spacing between the plates is not regulated by the spacers The term "closed configuration" of the two plates in a QMAX process means a configuration in which the plates are facing each other, the spacers and a relevant volume of the sample are between the plates, the relevant spacing between the plates, and thus the thickness of the relevant volume of the sample, is regulated by the plates and the spacers, wherein the relevant volume is at least a portion of an entire volume of the sample.

The term "a sample thickness is regulated by the plate and the spacers" in a QMAX process means that for a give condition of the plates, the sample, the spacer, and the plate compressing method, the thickness of at least a port of the sample at the closed configuration of the plates can be predetermined from the properties of the spacers and the plate.

The term "inner surface" or "sample surface" of a plate in a QMAX device refers to the surface of the plate that touches the sample, while the other surface (that does not touch the sample) of the plate is termed "outer surface".

The term "height" or "thickness" of an object in a QMAX process refers to, unless specifically stated, the dimension of the object that is in the direction normal to a surface of the plate. For example, spacer height is the dimension of the spacer in the direction normal to a surface of the plate, and the spacer height and the spacer thickness means the same thing.

The term "area" of an object in a QMAX process refers to, unless specifically stated, the area of the object that is parallel to a surface of the plate. For example, spacer area is the area of the spacer that is parallel to a surface of the plate.

The term of QMAX device refers the device that perform a QMAX (e.g. CROF) process on a sample, and have or not have a hinge that connect the two plates.

In some embodiments of QMAX cards, they do not use spacers to control the sample thickness in a closed configuration of the movable plates, rather they use other ways to measure the sample thickness after reaching a closed configuration. The thickness measurements include light interference measurements.

C. Chemicals for Colorimetric Assays

As used herein the term "colorimetric" and grammatical variants thereof refer to the physical description and quantification of the color spectrum including the human color perception spectrum (e.g., visible spectrum). In some embodiments, a colorimetric assay is particularly useful when quantification is not necessary and where expensive detection equipment is unavailable. In certain embodiments, detection of the color change can be carried out by naked eye observation of a user (e.g., the person performing the assay). Because a colorimetric assay can be detected by naked eye observation, a user can either examine the reaction for a detectable change in color or the assay can be carried out in parallel with one or more controls (positive or negative) that replicate the color of a comparable reaction. In some embodiments, calibrated colorimetric measurements could be used to determine the amount of target quantitatively.

In general, a colorimetric analysis involves determining the presence/absence, level, or concentration of an analyte (such as a chemical element or chemical compound) in a sample, such as a solution, with the aid of a color reagent. It is applicable to both organic compounds and inorganic compounds and may be used with or without an enzymatic reaction step. Generally, the equipment required is a colorimeter, one or more cuvettes, and a suitable color reagent. The process may be automated, e.g., by the use of an AutoAnalyzer or by Flow injection analysis. In particular embodiments, colorimeters can be adapted for use with plate readers to speed up analysis and reduce the waste stream.

In one aspect, a colorimetric assay disclosed herein is a non-enzymatic method. For example, a metal ion can react with one or more agents to form one or more colored products. For instance, calcium can react with o-cresolphthalein complex one to form a colored complex; copper may react with bathocuproin disulfonate to form a colored complex; creatinine can react with picrate to form a colored complex; iron can react with bathophenanthroline disulfonate to form a colored complex; and phosphate can react with ammonium molybdate and/or ammonium metavanadate to form a colored complex.

In another aspect, a colorimetric assay disclosed herein comprises one or more enzymatic reaction step. Typically, the color reaction is preceded by a reaction catalyzed by an enzyme. As the enzyme is specific to one or more particular substrates, more accurate results can be obtained. For example, in an assay for cholesterol detection such as the CHOD-PAP method), cholesterol in a sample is first reacted with oxygen, catalyzed by the enzyme cholesterol oxidase), to produce cholestenone and hydrogen peroxide. The hydrogen peroxide is then reacted with 4-aminophenazone and phenol, this round catalyzed by a peroxidase, to produce a colored complex and water. Another example is the GOD-Perid method for detecting glucose, where glucose is a sample is first reacted with oxygen and water, catalyzed by the enzyme glucose oxidase, to generate gluconate and hydrogen peroxide. The hydrogen peroxide so generated then reacts with ABTS to produce a colored complex, and the reaction can be catalyzed by a peroxidase. In yet another example, the so-called GPO-PAP method detects triglycerides, which are first converted to glycerol and carboxylic acid (catalyzed by an esterase); the glycerol is then reacted with ATP to form glycerol-3-phosphate and ADP (catalyzed by a glycerol kinase); the glycerol-3-phosphate is then oxidized by a glycerol-3-phosphate oxidase to form dihydroxyacetone phosphate and hydrogen peroxide; and the final enzymatic reaction is catalyzed by a peroxidase, where the hydrogen peroxide reacts with 4-aminophenazone and 4-chlorophenol to form a colored complex. In some embodiments, the colorimetric assay may comprise both non-enzymatic step(s) and enzymatic step(s). For example, urea can be detected by first converting the analyte into ammonium carbonate (catalyzed by a urease), and then the ammonium carbonate reacts with phenol and hypochlorite in a non-enzymatic reaction to form a colored complex.

In some embodiments, a colorimetric assay detects a protein target. In one aspect, a colorimetric assay involves the formation of a protein-metal chelation (such as protein-copper chelation), followed by secondary detection of the reduced metal (e.g., copper). Examples of this type of colorimetric assay include the BCA assay and the Lowry protein assay, such as the Thermo Scientific Pierce BCA and Modified Lowry Protein Assays. In another aspect, a colorimetric assay involves protein-dye binding with direct detection of the color change associated with the bound dye. Examples of this type of colorimetric assay include the 660 nm assay and the Coomassie (Bradford) protein assay. Other examples of colorimetric assays for detecting a polypeptide or protein target include the Biuret assay, the Bicinchoninic Acid (Smith) assay, the Amido Black method, and the Colloidal Gold assay.

In particular embodiments, the colorimetric assay, such as a colorimetric screening, can be based on NAD(P)H generation. The absorbance of NAD(P)H at 340 nm is commonly used to measure the activity of dehydrogenases. Typically, this type of colorimetric assay involves an indirect method requiring either a synthetic compound or a secondary enzyme. For example, tetrazolium salts such as nitroblue tetrazolium (NBT) can be reduced to formazan dyes, which absorb light in the visible region. These reactions are essentially irreversible under biological conditions and the increase in color can be easily monitored visually on filter discs or on a standard 96-well plate reader. A cascade reaction leading to the formation of a colored formazan links the production of NAD(P)H to the catalytic activity of a dehydrogenase in a sample.

In particular embodiments, the colorimetric assay is an Enzyme-Linked Immunosorbent Assay (ELISA). Examples of colorimetric ELISA substrates include colorimetric (also called chromogenic) substrate for alkaline phosphatase (AP) and/or horseradish peroxidase enzyme (HRP), such as PNPP (p-Nitrophenyl Phosphate, a widely used substrate for detecting alkaline phosphatase in ELISA applications to produce a yellow water-soluble reaction product that absorbs light at 405 nm), ABTS (2,2'-Azinobis [3-ethylbenzothiazoline-6-sulfonic acid]-diammonium salt, which is used to detect HRP and yields a water-soluble green end reaction product), OPD (o-phenylenediamine dihydrochloride, which is used to detect HRP and yields a water soluble yellow-orange reaction product), and TMB (3,3',5,5'-tetramethylbenzidine, which yield a blue color when detecting HRP).

Specific examples of a colorimetric assay include the HRP/ABTS/H2O2 Assay, HRP/4CN/H2O2 Assay, the D-Amino Acid Oxidase Assay, the Peroxidase/o-Dianisidine Assay, the ABTS and o-Dianisidine Assay, the TMB Assay, the Guaiacol Assay, the MNBDH Assay, assays based on the Gibbs' Reagent and 4-Aminoantipyrine, the Poly R-478 Assay, the Horseradish Peroxidase-coupled Assay, the MTT assay, the Indole Assay, and the para-Nitrophenoxy Analog (pNA) Assay.

The devices and methods described above may be used to perform any one or more of the following colorimetric assays. Suitable colorimetric assays include, but are not limited to, colorimetric assays that detect proteins, nucleic acids, antibodies, or microorganisms. Colorimetric assays may be used to determine the concentration of a substance in a solution. In some cases, the colorimetric assays include colorimetric immunoassays. Suitable colorimetric assays may include those described in Jiang et al., *Analyst* (2016), 141: 1196-1208; Morbioli et al., *Anal. Chim. Acta*. (2017), 970: 1-22; Gu et al., *Biotechnology Advances* (2015), 33: 666-690; Marin et al., *Analyst*. (2015), 140(1): 59-70; Du et al., *Small*. (2013), 9 (9-10): 1467-81; Song et al., *Adv. Mater*. (2011), 23 (37):4215-36; Liu et al., *Nanoscale* (2011), 3(4):1421-33; Martin et al. *J. Animicrob Chemother*. (2007) 59 (2): 175-83; Sapan et al. *Biotechnol. Appl. Biochem*. (1999), 29(pt 2): 99-108.

Colorimetric immunoassays can include enzyme immunoassays such as, e.g., an enzyme-linked immunosorbent assay (ELISA). ELISA assays can include labeling a surface bound antigen with an enzyme, e.g., with a single antibody conjugate or two or more antibodies working in concert to label the antigen with the enzyme. An antigen may be immobilized on a solid surface by non-specific means (e.g., adsorption) or by specific means (e.g., capture by an antibody, in a "sandwich" ELISA). The incubation can be followed by washing steps and the addition of a detection antibody covalently linked to an enzyme. In some cases, the detection antibody is a primary antibody that is itself detected by a secondary antibody linked to an enzyme. Following labeling of the enzyme, and typically after one or more washing steps, the enzyme is reacted with an appropriate substrate, such as a chromogenic substrate, in such a manner as to produce a signal, e.g., a chemical signal, that may be detected, e.g., by spectrophotometric, fluorimetric or by visual means. Such color change may indicate the presence and/or quantity of the antigen in the sample. Types of ELISA assays include, for example, direct ELISA, sandwich ELISA, and competitive ELISA.

Suitable enzymes for use in enzyme immunoassays include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection in such assays can be accomplished by colorimetric methods which employ a chromogenic substrate for the enzyme, where suitable substrates include, but are not limited to: o-phenylenediamine (OPD), 3,3',5,5'-tetramethylbenzidine (TMB), 3,3'-diaminobenzide tetrahydrochloride (DAB), 2,2'-azino-bis(3-ethylbenzthiazoline-6-sulphonic acid) (ABTS), and the like. A fluid composition of the substrate, e.g., an aqueous preparation of the substrate, is typically incubated with the substrate surface for a period of time sufficient for the detectable product to be produced. Incubation typically lasts for a period of time ranging from about 10 sec to 2 hours, usually from about 30 sec to 1 hour and more usually from about 5 min to 15 min at a temperature ranging from about 0 to 37° C., usually from about 15 to 30° C. and more usually from about 18 to 25° C.

Colorimetric immunoassays can include lateral flow assays (LFA) or immunochromatography assays. Such assays may be performed on a series of capillary beds, e.g., porous paper or polymers, for transporting fluid. Conventional lateral flow test strips include a solid support on which a sample receiving area and the target capture zones are supported. The solid support material is one which is capable of supporting the sample receiving area and target capture zones and providing for the capillary flow of sample out from the sample receiving area to the target capture zones when the lateral flow test strip is exposed to an appropriate solvent or buffer, which acts as a carrier liquid for the sample. General classes of materials which may be used as supports include organic or inorganic polymers, and natural and synthetic polymers. More specific examples of suitable solid supports include, without limitation, glass fiber, cellulose, nylon, crosslinked dextran, various chromatographic papers and nitrocellulose.

At the capture zones, capture molecules may bind the complex, producing a color change in the test strip. The capture zones may include one or more components of a signal producing system. The signal producing system may vary widely depending on the particular nature of the lateral flow assay and may be any directly or indirectly detectable label. Suitable detectable labels for use in the LFA include any moiety that is detectable by spectroscopic, photochemical, biochemical, immunochemical, electrical, optical, chemical, or other means. For example, suitable labels include biotin for staining with labeled streptavidin conjugate, fluorescent dyes (e.g., fluorescein, Texas red, rhodamine, green fluorescent protein, and the like), radiolabels (e.g. $^{3}H$, $^{125}I$, $^{35}S$, $^{1}C$, or $_{32}$), enzymes (e.g., horseradish peroxidase, alkaline phosphatase and others commonly used in an ELISA), and colorimetric labels such as colloidal gold nanoparticles, silver nanoparticles, magnetic nanoparticles, cerium oxide nanoparticles, carbon nanotubes, graphene oxide, conjugated polymers, or colored glass or plastic (e.g., polystyrene, polypropylene, latex beads). Radiolabels can be detected using photographic film or scintillation counters, fluorescent markers can be detected using a photodetector to detect emitted light. Enzymatic labels are typically detected by providing the enzyme with a substrate and detecting the reaction product produced by the action of the enzyme on the substrate, and colorimetric labels are detected by simply visualizing the colored label.

In some cases, the colorimetric assay may be used to measure ions in a sample. For example, chloride ions can be measured by a colorimetric assay. Chloride ions displace thiocyanate from mercuric thiocyanate. Free thiocyanate reacts with ferric ions to form a colored complex—ferric thiocyanate, which is measured photometrically.

Likewise, magnesium can be measured colorimetrically using calmagite, which turns a red-violet color upon reaction with magnesium; by a formazan dye test; emits at 600 nm upon reaction with magnesium or using methylthymol blue, which binds with magnesium to form a blue colored complex.

Likewise, calcium can be detected by a colorimetric technique using O-Cresolphtalein, which turns a violet color upon reaction of 0-Cresolphtalein complexone with calcium.

Likewise, bicarbonate can be tested bichromatically because bicarbonate ($HCO_3^-$) and phosphoenolpyruvate (PEP) are converted to oxaloacetate and phosphate in the reaction catalyzed by phosphoenolpyruvate carboxylase (PEPC). Malate dehydrogenase (MD) catalyzes the reduction of oxaloacetate to malate with the concomitant oxidation of reduced nicotinamide adenine dinucleotide (NADH). This oxidation of NADH results in a decrease in absorbance of the reaction mixture measured bichromatically at 380/410 nm proportional to the Bicarbonate content of the sample. Blood urea nitrogen can be detected in a colorimetric test in which diacetyl, or fearon develops a yellow chromogen with urea and can be quantified by photometry. Likewise, creatinine can be measured colorimetrically, by treated the sample with alkaline picrate solution to yield a red complex. In addition, creatine can be measured using a non-Jaffe reaction that measures ammonia generated when creatinine is hydrolyzed by creatinine iminohydrolase. Glucose can be measured in an assay in which blood is exposed to a fixed quantity of glucose oxidase for a finite period of time to estimate concentration. After the specified time, excess blood is removed and the color is allowed to develop, which is used to estimate glucose concentration. For example, glucose oxidase reaction with glucose forms nascent oxygen, which converts potassium iodide (in the filter paper) to iodine, forming a brown color. The concentration of glycosylated hemoglobin as an indirect read of the level of glucose in the blood.

Plasma high-density lipoprotein cholesterol (HDL-C) determination is measured by the same procedures used for plasma total cholesterol, after precipitation of apoprotein B-containing lipoproteins in whole plasma (LDL and VLDL) by heparin-manganese chloride. These compounds can also be detected colorimetrically in an assay that is based on the enzyme driven reaction that quantifies both cholesterol esters and free cholesterol. Cholesterol esters are hydrolyzed via cholesterol esterase into cholesterol, which is then oxidized by cholesterol oxidase into the ketone cholest-4-en-3-one plus hydrogen peroxide. The hydrogen peroxide is then detected with a highly specific colorimetric probe. Horseradish peroxidase catalyzes the reaction between the probe and hydrogen peroxide, which bind in a 1:1 ratio. Samples may be compared to a known concentration of cholesterol standard.

Examples of Reagents
A. Glucose Colorimetric (Fluorimetric) Assay
Sample: Whole Blood, Plasma, Serum, Saliva
Reagent Recipe 1:
100 units/ml Glucose Oxidase, 100 unit/ml Horseradish Peroxidase, 20 mM 4-amino antipyrine, 20 mM TOOS
Reagent Recipe 2:
100 unit/ml Glucose Oxidase, 100 unit/ml Horseradish Peroxidase, 20 mM 3,5,3',5'-Tetramethylbenzidine (TMB)
Reagent Recipe 3:
100 unit/ml Glucose Oxidase, 100 unit/ml Horseradish Peroxidase, 20 mM Amplex Red
Reagent Recipe 4:
1 unit/ml Hexokinase, 220 mg/ml ATP, 400 mg/ml NAD
B. Calcium Colorimetric Assay
Sample: Whole Blood, Plasma, Serum, Saliva
Reagent Recipe 1:
17 mg/ml Arsenazo III
C. Albumin Colorimetric Assay
Sample: Whole Blood, Plasma, Serum, Saliva
Reagent Recipe 1:
22 mg/ml Bromcresol purple
D. Total Protein Colorimetric assay
Sample: Whole Blood, Plasma, Serum, Saliva
Reagent Recipe 1:
1.34 mg/ml Cupric sulfate, 3.43 mg/ml Sodium potassium tartrate, 0.28 mg/ml Potassium iodide
E. Sodium Colorimetric Assay
Sample: Whole Blood, Plasma, Serum, Saliva
Reagent Recipe 1:
220 mg/ml ONPG, 0.05 unit/ml β-Galactosidase
F. Potassium Colorimetric Assay
Sample: Whole Blood, Plasma, Serum, Saliva
Reagent Recipe 1:
220 mg/ml ADP, 0.05 unit/ml Phosphoenolpyruvate, 0.1 unit/ml Pyruvate kinase, 480 mg/ml NADH, 13.6 mg/ml Potassium phosphate, 95 mg/ml Magnesium sulfate, 7.85 mg/ml FAD, 130 mg/ml 4-Aminoantipyrine, 10 unit/ml Horseradish Peroxidase, 1.88 mg/ml TBHBA
G. Chloride Colorimetric Assay
Sample: Whole Blood, Plasma, Serum, Saliva
Reagent Recipe 1:
530 mg/ml CNPG3, 0.36 unit/ml α-Amylase, 250 mg/ml Calcium acetate
H. Blood Urea Nitrogen Colorimetric Assay
Sample: Whole Blood, Plasma, Serum, Saliva
Reagent Recipe 1:
0.5 U/ml Urea Amidolyase, 570 ug/ml PEP, 220 ug/ml ATP, 1 U/ml Pyruvate Kinase 10U/ml Pyruvate Oxidase, 13.6 mg/ml Potassium phosphate, 95 ug/ml $MgCl_2$, 7.85 ug/ml FAD
1.88 mg/ml TBHBA, 130 ug/ml 4-AAP, 10 U/ml Peroxidase
I. Creatinine Colorimetric Assay
Sample: Whole Blood, Plasma, Serum, Saliva
Reagent Recipe 1:
10 U/ml Creatinine Amidohydrolase, 30 U/ml Creatinine Amidinohydrolase, 10 U/ml Sarcoosine Oxidase, 1.88 mg/ml TBHBA, 130 ug/ml 4-AAP, 10 U/ml Peroxidase
J. Alkaline Phosphatase Colorimetric Assay
Sample: Whole Blood, Plasma, Serum, Saliva
Reagent Recipe 1:
560 ug/ml p-Nitrophenyl Phosphate, 0.5 U/ml Zinc Sulfate, 330 ug/ml Magnesium Sulfate K. Alanine Amino Transferase Colorimetric Assay
Sample: Whole Blood, Plasma, Serum, Saliva
Reagent Recipe 1:
8.74 mg/ml L-Alanine, 1.01 mg/ml α-Ketoglutaric Acid 10U/ml Pyruvate Oxidase, 13.6 mg/ml Potassium phosphate, 95 ug/ml MgCl2, 7.85 ug/ml FAD, 1.88 mg/ml TBHBA, 130 ug/ml 4-AAP, 10 U/ml Peroxidase L. Aspartate Amino Transferase Colorimetric Assay
Sample: Whole Blood, Plasma, Serum, Saliva
Reagent Recipe 1:
4.26 mg/ml L-Aspartic Acid, 1.01 mg/ml α-Ketoglutaric Acid, 10 U/ml Oxaloacetate decarboxylase, 1.88 mg/ml TBHBA, 130 ug/ml 4-AAP, 10 U/ml Peroxidase M. Bilirubin Colorimetric Assay
Sample: Whole Blood, Plasma, Serum, Saliva
Reagent Recipe 1:
1 U/ml Bilirubin Oxidase N. Cholesterol Colorimetric (Fluorimetric) Assay
Sample: Whole Blood, Plasma, Serum, Saliva
Reagent Recipe 1:
100 unit/ml Cholesterol Oxidase, 100 unit/ml Horseradish Peroxidase, 20 mM 4-amino antipyrine, 20 mM TOOS
Reagent Recipe 2:
100 unit/ml Cholesterol Oxidase, 100 unit/ml Horseradish Peroxidase, 20 mM 3,5,3',5'-Tetramethylbenzidine (TMB)
Reagent Recipe 3:
100 unit/ml Cholesterol Oxidase, 100 unit/ml Horseradish Peroxidase, 20 mM Amplex Red O. Triglycerides Colorimetric (Fluorimetric) Assay
Sample: Whole Blood, Plasma, Serum, Saliva
Reagent Recipe 1:
100 unit/ml Lipase, 100 unit/ml Glycerokinase, 100 unit/ml Glycerophosphate Oxidase, 20 mM 4-amino antipyrine, 20 mM TOOS
Reagent Recipe 2:
100 unit/ml Lipase, 100 unit/ml Glycerokinase, 100 unit/ml Glycerophosphate Oxidase, 20 mM 3,5,3',5'-Tetramethylbenzidine (TMB)
Reagent Recipe 3:
100 unit/ml Lipase, 100 unit/ml Glycerokinase, 100 unit/ml Glycerophosphate Oxidase, 20 mM Amplex Red P. Alcohol Colorimetric (Fluorimetric) Assay
Sample: Whole Blood, Plasma, Serum, Saliva, Breath
Reagent Recipe 1:
100 unit/ml Alcohol Oxidase, 100 unit/ml Horseradish Peroxidase, 20 mM 4-amino antipyrine, 20 mM TOOS
Reagent Recipe 2:
100 unit/ml Alcohol Oxidase, 100 unit/ml Horseradish Peroxidase, 20 mM 3,5,3',5'-Tetramethylbenzidine (TMB)
Reagent Recipe 3:
100 unit/ml Alcohol Oxidase, 100 unit/ml Horseradish Peroxidase, 20 mM Amplex Red Q. Hydrogen Peroxide (Fluorimetric) Assay
Sample: Whole Blood, Plasma, Serum, Saliva, Breath
Reagent Recipe 1:
100 unit/ml Horseradish Peroxidase, 20 mM 4-amino antipyrine, 20 mM TOOS
Reagent Recipe 2:
100 unit/ml Horseradish Peroxidase, 20 mM 3,5,3',5'-Tetramethylbenzidine (TMB)
Reagent Recipe 3:
100 unit/ml Horseradish Peroxidase, 20 mM Amplex Red R. Gram Staining
Sample: Blood smear, Vaginal samples, Genital samples
Gram Crystal Violet
20 g Crystal Violet, 8 g Ammonium Oxalate, 200 mL Methanol
Gram Iodine
3.33 g Iodine Crystal, 6.67 g Potassium Iodide
Gram Decolorizer
500.0 mL Ethanol, 500.0 mL Acetone
Gram Safranin
0.25 g Safranin O, 10 mL Ethanol
Gram Basic Fuchsin Basic
0.7 g Fuchsin, 3.5 mL Phenol, 14 mM Ethanol S. Leishman Staining
Sample: Smear sample
Recipe 1
0.2 g Leishman's dye, 100 mL Acetone-free methyl alcohol T. Giemsa Staining
Sample: Smear sample
Recipe 1
0.15 g Giemsa powder, 12.5 mL Glycerin, 12.5 mL Methyl alcohol U. Wright Staining
Sample: Smear sample
Recipe 1
1.5 g Wright stain, 500 mL Methanol V. Field Staining
Sample: Smear sample
Field Solution A
1.6 g Methylene Blue, 10 g Disodium dihydrogen phosphate, 12.5 g Potassium dihydrogen phosphate, 1g Azur, 1000 mL Distilled water
Field Solution B
2 g Eosin Y, 10 g Disodium dihydrogen phosphate, 12.5 g Potassium dihydrogen phosphate,
1000 mL Distilled water W. Jenner Staining
Sample: Smear sample
Recipe 1
0.5 g Jenner stain, 100 mL Methanol X. JSB Staining
Sample: Smear sample
Recipe 1
0.5 g Atine orange dye, 3 mL 1% Sulfuric acid, 0.5 g Potassium dichromate, 3.5 g Disodium hydrogen phosphate dehydrate, 500 mL Distilled water
JSB stain II
1 g Eosin Y, 500 ml Distilled water Y. White Blood cells staining for counting and differentiate
Sample: Blood, urine, other body fluidics
Recipe 1
1 ug/mL to 1 mg/mL Acridine Orange (Detection agents)
Recipe 2
150 uM Propidium Iodide (PI) (Detection agents), 100 uM Fluorescein Isothiocyanate (FITC), 250 uM Basic Orange 21 (BO21) dye Z. Platelets Staining for Counting
Sample: Blood, urine, other body fluidics
Recipe 1
1 ug/mL to 1 mg/mL Acridine Orange (Detection agents)
Recipe 2
150 uM Propidium Iodide (PI) (Detection agents), 100 uM Fluorescein Isothiocyanate (FITC),
250 uM Basic Orange 21 (BO21) dye Testing System with QMAX Device One aspect of the present invention provides systems and methods of analyzing a bio/chemical sample using QMAX device.

AA1. A method for analyzing a sample, comprising:
- a) depositing a sample on a Q-card and closing the Q-card;
- b) inserting the closed Q-card into an adaptor that connects to a camera of a handheld mobile communication device;
- c) taking image(s) of the closed Q-card using the camera of the handheld mobile communication device;
- d) transmitting, to a remote location, the image(s) and/or an analysis result of the images from the handheld mobile communication device;
- e) analyzing, at the remote location, the image(s) and/or the analysis result transmitted from the mobile communication device; and
- f) notifying a third party and/or the handheld mobile communication device if an anomaly is detected;

wherein the Q-card comprises two plates that are movable relative to each other and have an open configuration and a closed configuration;

wherein the sample is deposited on one or both plates of the Q-Card at the open configuration, and at the closed configuration at least a part of the sample is between the two plates, wherein the mobile communication device is configured to produce an image of the Q card in the adaptor and transmit the image and/or an analysis result of the same to a remote location.

AA2. The method of any prior embodiment, wherein the sample deposited onto the Q-card is from a subject, and the subject performs step a).

AA3. The method of any prior embodiment, wherein the anomaly is identified if the analysis result of the sample is not within a normal range.

AA4. The method of any prior embodiment, wherein the anomaly is identified if the analysis results produced by the remote device and the mobile handheld communication device differ by a pre-defined value.

AA5. The method of any prior embodiment, wherein the sample comprises a body fluid selected from the group consisting of: amniotic fluid, aqueous humour, vitreous humour, blood (e.g., whole blood, fractionated blood, plasma, serum, etc.), breast milk, cerebrospinal fluid (CSF), cerumen (earwax), chyle, chime, endolymph, perilymph, feces, gastric acid, gastric juice, lymph, mucus (including nasal drainage and phlegm), pericardial fluid, peritoneal fluid, pleural fluid, pus, rheum, saliva, sebum (skin oil), semen, sputum, sweat, synovial fluid, tears, vomit, urine and exhaled condensate.

AA6. The method of any prior embodiment, wherein the sample comprises an environmental specimen that is obtained from: river, lake, pond, ocean, glaciers, icebergs, rain, snow, sewage, reservoirs, tap water, drinking water, soil, compost, sand, rocks, concrete, wood, brick, sewage; air, heat vents, industrial exhaust, or vehicular exhaust.

AA7. The method of any prior embodiment, wherein the sample comprises a foodstuff specimen that includes: raw food ingredients, cooked or processed food, plant and animal sources of food, preprocessed food, or fully processed food.

AA8. The method of any prior embodiment, wherein, in step (a), the Q-card is pressed by human hand.

AA9. The method of any prior embodiment, wherein step e) comprises comparing the result to a threshold or normal range to identify samples that contain an anomaly.

AA10. The method of any prior embodiment, wherein the method further comprises updating the handheld mobile communication device if the analysis at the remote location produces a result that is significantly different.

AA11. The method of any prior embodiment, wherein the sample deposited onto the Q-card is from a subject, and the analysis result is not transmitted to the subject.

AA12. The method of any prior embodiment, wherein the third party is a medical professional.

AA13. The method of embodiment AA12, wherein the medical professional is a doctor or nurse practitioner.

AA14. The method of any of embodiments AA1-AA12, wherein third party is an insurance company.

AA15. The method of any prior embodiment, wherein the result from the mobile communication device and/or the result from the remote location are sent to an emergency room.

AA16. The method of embodiment AA1, wherein, based on the results, the handheld mobile communication device or the remote location transmits follow-up information to the subject.

AA17. The method of embodiment AA16, wherein the follow-up information comprises an explanation of the result, education about a disease or condition, information related to a possible treatment, information on the location of a suitable physician, information related to change of diet and/or exercises, or an advertisement.

AA18. The method of any prior embodiment, wherein the Q-card comprises spacers that have a substantially uniform height and a predetermined constant inter spacer distance, and in the closed configuration: at least part of the sample is compressed by the two plates of the Q-card into a layer of highly uniform thickness and is substantially stagnant relative to the plates, wherein the uniform thickness of the layer is confined by the inner surfaces of the two plates and is regulated by the plates and the spacers.

AA19. The method of embodiment AA18, wherein at least one of the plates is flexible.

AA20. The method of embodiment AA19, wherein for the flexible plate, the thickness of the flexible plate times the Young's modulus of the flexible plate is in the range 60 to 750 GPa-um.

AA21. The method of embodiment AA19, wherein for the flexible plate, the fourth power of the inter-spacer-distance (ISD) divided by the thickness of the flexible plate (h) and the Young's modulus (E) of the flexible plate, ISD4/(hE), is equal to or less than 106 um3/GPa, AA22. The method of embodiment AA18, wherein spacers regulating the layer of uniform thickness have a filling factor of at least 1%, wherein the filling factor is the ratio of the spacer area in contact with the layer of uniform thickness to the total plate area in contact with the layer of uniform thickness.

AA23. The method of embodiment AA18, wherein for spacers regulating the layer of uniform thickness, the Young's modulus of the spacers times the filling factor of the spacers is equal or larger than 10 MPa, wherein the filling factor is the ratio of the spacer area in contact with the layer of uniform thickness to the total plate area in contact with the layer of uniform thickness.

AA24. The method of any prior embodiment, wherein one or both plates comprises a location marker, either on a surface of or inside the plate, that provide information of a location of the plate.

AA25. The method of any prior embodiment, wherein one or both plates comprises a scale marker, either on a surface of or inside the plate, that provide information of a lateral dimension of a structure of the sample and/or the plate.

AA26. The method of any prior embodiment, wherein one or both plates comprises an imaging marker, either on surface of or inside the plate, that assists an imaging of the sample.

AA27. The method of embodiment AA18, wherein the spacers functions as a location marker, a scale marker, an imaging marker, or any combination of thereof.

AA28. The method of embodiment AA18, wherein the average thickness of the layer of uniform thickness is in the range of 0.2 μm to 3.8 μm and the sample is blood.

AA29. The method of embodiment AA18, wherein the inter-spacer distance is in the range of 7 μm to 50 μm.

AA30. The method of embodiment AA18, wherein the inter-spacer distance is in the range of 50 μm to 120 μm.

AA31. The method of embodiment AA18, wherein the inter-spacer distance is in the range of 120 μm to 200 μm.

AA32. The method of embodiment AA18, wherein the inter-spacer distance is substantially periodic.

AA33. The method of embodiment AA18, wherein the spacers are pillars with a cross sectional shape selected from round, polygonal, circular, square, rectangular, oval, elliptical, or any combination of the same.

AA34. The method of embodiment AA18, wherein the spacers have are pillar shape and have a substantially flat top surface, wherein, for each spacer, the ratio of the lateral dimension of the spacer to its height is at least 1.

AA35. The method of embodiment AA18, wherein each spacer has the ratio of the lateral dimension of the spacer to its height is at least 1.

AA36. The method of embodiment AA18, wherein the minimum lateral dimension of spacer is less than or substantially equal to the minimum dimension of an analyte in the sample.

AA37. The method of embodiment AA18, wherein the minimum lateral dimension of spacer is in the range of 0.5 um to 100 um.

AA38. The method of embodiment AA18, wherein the spacers have a pillar shape, and the sidewall corners of the spacers have a round shape with a radius of curvature at least 1 μm.

AA39. The method of embodiment AA18, wherein the spacers have a density of at least 1000/mm2.

AA40. The method of any prior embodiment, wherein at least one of the plates is transparent.

AA41. The method of any prior embodiment, wherein at least one of the plates is made from a flexible polymer.

AA42. The method of embodiment AA18, wherein, for a pressure that compresses the plates, the spacers are not compressible and/or, independently, only one of the plates is flexible.

AA43. The method of any prior embodiment, wherein the flexible plate has a thickness in the range of 10 um to 200 um.

AA44. The method of embodiment AA18, wherein the variation of the uniform thickness is less than 30%.

AA45. The method of embodiment AA18, wherein the variation of the uniform thickness is less than 10%.

AA46. The method of embodiment AA18, wherein the variation of the uniform thickness is less than 5%.

AA47. The method of any prior embodiment, wherein the plates are connected by a hinge and are configured to be changed from the open configuration to the closed configuration by folding the plates along the hinge.

AA48. The method of any prior embodiment, wherein the layer of uniform thickness sample is uniform over a lateral area that is at least 1 mm2.

AB 1. A system for analyzing a sample, comprising:
  a) a Q-card for manipulating a sample for analysis comprising two plates that are movable relative to each other and have an open configuration and a closed configuration;
  b) a handheld mobile communication device that comprises a camera;
  c) an adaptor having a slot that is configured to hold a closed Q-Card, wherein the adaptor connects to the handheld mobile communication device and permits the camera to take an image of closed Q-Card; and
  d) a remote device that is capable of storing information and communicating with the mobile communication device;
    wherein the sample is deposited on one or both plates of the Q-Card at the open configuration, and at the closed configuration at least a part of the sample is between the two plates,
    wherein the system is configured to produce an image of the Q card in the adaptor and transmit the image and/or an analysis result of the same to a remote location.

AB2. The system of embodiment AB1, wherein the Q-card can be placed in the closed configuration by folding.

AB3. The system of embodiment AB1, wherein the remote device is configured to analyze the image and/or the analysis result of the same.

AB4. The system of embodiment AB1, wherein the remote device is configured to communicate with other remote devices.

AB5. The system of embodiment AB1, wherein the remote device is configured to notify a third if an anomaly in a sample placed in the Q card is detected.

AC1. A method for providing healthcare recommendations to a subject, comprising:
  a) using Q-cards and an associated mobile communication device to analyze one or a plurality of analytes in samples from a subject;
  b) transmitting, to a remote location, the analysis results of the analytes from the mobile communication device;
  c) storing the analysis results in a data set;
  d) generating, at the remote location, a series of healthcare recommendations based on accumulated analysis results in the data set; and
  e) providing the healthcare recommendations to the subject by sending messages to the mobile communication device;
  wherein the healthcare recommendations comprise suggestions related to medicine, nutrition/diet, exercise, and/or treatment for the subject.

AC2. The method of paragraph AC1, further comprising identifying the subject's needs before providing the healthcare recommendations to the subject.

B. Cholesterol Testing with QMAX Device

Another aspect of the present invention provides devices and methods of cholesterol testing using QMAX device.

BA1. A method of analyzing a liquid sample, comprising:
  (a) obtaining the liquid sample;
  (b) obtaining a device, which comprises a first plate, a second plate, and spacers fixed on one or both of the plates; wherein:
    i. the plates are movable relative to each other into different configurations, including an open configuration and a closed configuration;

ii. each plate respectively comprises an inner surface that has a sample contact area, and
iii. the spacers have a predetermined substantially uniform height, and at least one of the spacers is inside the sample contact area;
(c) depositing the sample on one or both of the plates when the plates are in an open configuration,
wherein in the open configuration the two plates are partially or entirely separated apart and the spacing between the plates is not regulated by the spacers; and
(d) after (c), bringing the two plates together and pressing the plates into a closed configuration,
wherein in the closed configuration: at least part of the sample is compressed by the two plates into a layer of highly uniform thickness, which is confined by the inner surfaces of the two plates and is regulated by the spacers;
wherein one or both sample contact surfaces comprise one or more storage sites that store one or more reagents, which are configured to dissolve and diffuse in the sample in the closed configuration, and react with cholesterol in the sample to produce or alter a luminescence signal;
(e) reading the luminescence signal from the layer of highly uniform thickness, thereby obtaining a measurement of total cholesterol in the sample.

BA2. The method of paragraph BA1, wherein the one or more reagents are configured to react with cholesterol to generate or alter a colormetric luminescence signal, wherein the reading step (e) comprises detecting and quantifying the colormetric luminescence signal from the analyte in the layer of highly uniform thickness.

BA3. The method of paragraph BA1, wherein the one or more reagents comprise cholesteryl ester hydrolase and cholesterol oxidase.

BA4. The method of paragraph BA3, wherein the one or more reagents further comprise peroxidase and a color probe.

BA5. The method of paragraph BA4, wherein the color probe comprises 4-aminophenazone and phenol.

BA6. The method of paragraph BA1, wherein the one or more storage sites comprise a first storage site located on the first plate and a second storage site located on the second plate.

BA7. The method of paragraph BA6, wherein:
i. the first storage site comprises cholesteryl ester hydrolase and cholesterol oxidase; and
ii. the second storage site comprises 4-aminophenazone, phenol and peroxidase.

C. Heavy Metal Testing

Another aspect of the present invention provides devices and methods of heavy metal testing in bio/chemical samples. More specifically, the invention provides a process for detecting heavy metal ions in an aqueous system, a device comprising the heavy metal ion test piece and a sensor. A portable test method provided by the device according to the invention, so as to detect the heavy metal ions in a convenient, efficient and rapid manner.

The heavy metal (ion) pollution refers to the environmental pollution caused by heavy metals or their compounds. The increase of the heavy metal content in the environment, especially in the case of heavy metal pollution in an aqueous system, is mainly due to human factors, such as mining, waste gas emission, sewage irrigation and the use of heavy metal-containing products, which results in the deterioration of environmental quality. Currently there is still a need for a heavy metal ion test piece which can be used to detect the small amount, even trace amount of heavy metal ions in an aqueous system in a simple, low cost, highly sensitive, highly reliable and stable manner. Meanwhile, it is required that the test piece is available for in situ detection, and is capable of detecting heavy metal ions with high sensitivity. Moreover, it is desired that the heavy metal ions can be not only qualitatively detected, but also quantitatively or semi-quantitatively detected. The current invention provides devices and methods for achieving these goals.

C-1. Devices and Methods for Heavy Metal Testing

FIG. C1 shows that the invention comprises two parts: 1. Test, which comprises a test card that has dried reagent in a volume-controlled sample chamber, and can be inserted into a smartphone-based reader for measurement; 2. Calculation, which comprises a method to convert the photograph taken by smartphone and convert to signal for calculating analyte concentrations.

As demonstrated by FIG. C1, this invention is a device and method for obtaining a point-of-collection, selected quantitative indicia of an analyte on a test platform, comprising:
1. providing a modular, colorimetric reactive test platform having a test region and calibration region;
2. providing an analyte to be tested on the test region of the modular, colorimetric test platform, wherein the test region is adapted to enable a colorimetric reaction to the analyte;
3. obtaining a color image of the test region containing the analyte and the calibration region;
4. selecting an array of pixels in each of the color images of the test region containing the analyte and the calibration region;
5. determining a median RGB color value for each of the arrays of pixels;
6. converting the median RGB color value for each of the arrays of pixels to a characteristic value;
7. providing a calibration indicia that relates a selected quantitative indicia of the characteristic value;
8. associating the characteristic value to determine the selected quantitative indicia of the analyte As shown in FIG. C2, a first plate, which is a coerce white substrate, is printed uniformly with color indicator as well as pH regulating agent. The color indicator is bio/chemical reagent that shows specific reaction to heavy metals in liquid sample. The liquid sample includes, but is not limited to, water, soil sample, oil, body fluid and food. In certain embodiments, the sample is drinking water. In certain embodiments, the sample is food. In some embodiments, the first plate is a coerce white polystyrene plate. In some embodiments, the color indicator is dried on the first plate. In some embodiments, the pH regulating agent is dried on the first plate. In some embodiments, the concentration of dried color indicator is 1 uM to 10 mM. In some embodiments, the concentration of dried pH regulating agent is 1 uM to 10 mM.

As shown in FIG. C2, the surface of the first plate facing the second plate is defined as the inner surface of the first plate; the surface of the second plate that faces the first plate are also defined as the inner surface of the second plate. In some embodiments, the inner surfaces of the respective plates comprise a sample contact area for contacting a sample that comprises an analyte. The sample contact area can occupy part or the entirety of the respective inner surface.

As shown in FIG. C2, for testing heavy metal in water using colorimetric tests, a pH regulating agent must add to the sample to adjust the pH level to optimum condition. This is because the chemical reaction rate of color indicator to heavy metal ions changes significantly at different pH level, which leads to large color variation within tests if the pH is unregulated. For heavy metal test, a pH regulating agent, or a combination of multiple combination of them, is dried on the plate for adjusting sample PH level includes, but is not limited to: Formic acid (methanoic acid), Oxalic acid (ethanedioic acid), Lactic acid (2-hydroxypropanoic acid), Malic acid (2-hydroxybutanedioic acid), Citric acid (2-hydroxypropane-1,2,3-tricarboxylic acid), Carbonic acid (hydroxymethanoic acid, not an IUPAC name), Aminomethylphosphonic acid.

As shown in FIG. C2, the second plate comprises spacers that are fixed on the inner surface of the second plate. It should be noted, however, that in some embodiments the spacers are fixed on the inner surface of the first plate and in other embodiments on the inner surfaces of both the second plate and the first plate As shown in FIG. C2, the spacer is between 1 um, 2 um, 5 um, 10 um, 20 um, 50 um, 100 um, 200 um, 500 um, 1000 um or in a range between any of the two values. The diameter of hole in the spacer is around 0.5 mm, 1 mm, 2 mm, 3 mm 4 mm, 5 mm, or in a range between any of the two values. The center-to-center spacing between holes is 1 mm, 2 mm, 3 mm, 4 mm, 5 mm, 6 mm, 7 mm, 8 mm, 9 mm, 10 mm, 20 mm, 50 mm. or in a range between any of the two values. The second plate is a transparent flat film, with thickness around 1 um, 2 um, 5 um, 10 um, 20 um, 50 um, 100 um, 200 um, 500 um, 1000 um or in a range between any of the two values.

As shown in FIG. C2, the first plate and the second plate are moveable relative to each other into different configuration. One of the configurations is an open configuration, in which the two plates are partially or entirely separated apart and the spacing between the plates are not regulated by the spacers. FIG. C1 shows the plates in the open configuration, in which a sample, such as but not limited to blood, can be added to first plate, the second plate, or both of the plates. In some embodiments, the inner surface of a respective plate comprises a sample contact area, which occupies a part of the entirety of the inner surface. In certain embodiments, the spacers are positioned within the sample contact area. In some embodiments, the spacers are not fixed to any one of the plates, but are mixed in the sample.

As shown in FIG. C2 The second plate is a transparent thin film with smooth surface. It is necessary that the absorption of second plate does not interfere with the absorption of color indicator. Depends on the flexibility of the material, thickness from 10 um~300 um can be used as second plate, as long as no distortion of sample chamber will happen after second plate is pressed onto the sample.

FIG. 3 shows a Schematics of test procedure. 1. First, minute samples are added to each well printed with color indicator and and pH regulating agent. 2. The transparent second plate is then pressed on top of the spacer to form a closed sample chamber. 3. Incubation about 1 min to allow each individual sample to develop color. In this process, the color indicator and pH regulating agent is fully dissolved and mixed.

As shown in FIG. C3, a white polystyrene (PS) substrate printed with home-made color indicator and pH regulating agent. The color indicator and pH regulating agent amount on the sensing area is carefully controlled according to the dimension of the well, so that when each well is filled full with sample, the desired pH level and color indicator concentration can be achieved. Depends on the type of heavy metal or their combinations, different chemicals are used as color indicator. Color Indicator can be: (1) For lead detection, the color indicator is 0.01%~0.2% Sodium Rhodizonate (preferable 0.2% after dissolved in sample), or (2) For Copper, Cadmium, Chromium, Mercury, 10 uM~1 mM Dithizone (preferable 30 uM after dissolved in sample)

As shown in FIG. C3, the printing parameter for Color Indicator agent can vary as long as uniform drying is achieved on the first plate. The printing conditions, i.e., droplet volume, speed, depends on the surface wetting property of the first plate, which is well-known to skilled person, thus do not require elucidation. In this invention, the printing condition is droplet diameter 500~600 um, pitch~1 mm, print speed~10 mm/sec.

As shown in FIG. C3, the well dimension is determined by dimensions of holes array on the spacer. The thickness of the spacer, the diameter of the holes and their spacing determines the sample volume. Their configuration is flexible but it is crucial to avoid distortion of sample chamber under certain configurations, i.e. small aspect ratio. Here, the thickness of the spacer can be 2 um~1 mm (preferably 100 um), and the well diameter can be 100 um~10 mm (preferably, 3 mm), and the center-to-center spacing can be 100 um~10 mm, (preferably, 6 mm).

As shown in FIG. C3, In some embodiments, the method of the present invention, after step (2) and before step (3), further comprise incubating the layer of uniform thickness for a predetermined period of time. In certain embodiments, the predetermined period of time is equal to or longer than the time needed for the detection antibody to diffuse into the sample across the layer of uniform thickness. In certain embodiments, the predetermined period of time is less than 10 seconds, 20 seconds, 30 seconds, 45 seconds, 1 minute, 1.5 minutes, 2 minutes, 3 minutes, 4 minutes, 5 minutes, 6 minutes, 7 minutes, 8 minutes, 9 minutes, 10 minutes, 15 minutes, 20 minutes, 30 minutes, or 60 minutes, or in a range between any of the two values.

FIG. C4 shows the diagram of a chemical reaction that is used to test lead in water. The lead ion reacts with Sodium Rhodizonate (dark yellow color) dissolved in sample, which form a insoluble lead Rhodizonate that has a red-crimson color. The color absorption can be analyzed to calculate the lead concentration in water.

FIG. C5 A diagram of a chemical reaction that is used to test heavy metals in water. The heavy metals can be Cd, Cu, Cr, Hg. The heavy metal ion reacts with Dithiozone dissolved in sample, which form a Dithizone-Metal complex that yield a different color for different heavy metals. The color can be used to identify the type of heavy metals and the color absorption can be analyzed to calculate the heavy metal concentration in water.

FIG. C6 shows schematics of converting colorimetric Lead in water test standard curve of individual R, G, B channel to a single standard curve. For each sample contains different concentration of heavy metals, the R, G, B signal are different. A combination of R, G, B channel signal at different Lead concentration is used for this conversion. In some embodiment, the method of combination is linear combination. In some embodiment, the coefficient for combining RGB channel signal, is a constant. In some embodiment, the coefficient for combining RGB channel signal, is a matrix. In some embodiment, the coefficient for combining RGB channel signal, is a function of lead concentration in water.

As shown in FIG. C7 the algorithm to converting standard curve of individual R, G, B channel to a single standard curve is a process to find the best coefficient of combing R,G,B signals so that best sensitivity of assay can be achieved. In some embodiment, a linear combination of R, G, B channel signal at different Lead concentration is used for this conversion. In some embodiment, the linear coefficient is trained using a Generalized Reduced Gradient Algorithm. Such algorithm is open source and known to skilled person and does not require elucidation. Here, the process of this algorithm is shown in a diagram, briefly:

1. First, we define 4 constant: C1, C2, C3, and C4 so that Signal=$C_1*R+C_2G+C_3*B+C_4$
2. Change the linear coefficient by a small amount with pre-defined amount
3. Calculate the limit of detection (LOD),
4. keep changing the linear coefficient until the minimum LOD can be achieved In this invention, we trained the data using 48 different tests. It is expected that the precision can be further improved with more training data. This well known among skilled person and does not require further elucidation.

C-2. Example: Test Lead Concentration in Tap Water

As an example, we Prepare a chip for testing lead in water. On a white coerce PS substrate we printed with home-made color indicator. The color Indicator is 0.2% Sodium Rhodizonate (this is the saturated concentration) and the pH regulating agent is pH~3.0 by adding citric acid (this pH was optimized by our own experiment). We printed the reagent mixture with a parameter of droplet diameter 500~600 um, pitch~1 mm and Print speed 10 mm/sec.

For this example, we fabricated a plate, each plate has 48 wells, well diameter is 3 mm Center-to-center distance is 6 mm, well height is ~100 um (controlled using double-sided tape from Adhesive Research). We then drop 0.7 uL of sample in each well. Then we cover the well using 175 um thick PET film and wait for 1 min. Each well is immediately measured after 1 min incubation. For the test, the light source used is the smartphone camera flash light. And the image is taken using the smartphone's camera.

As assay validation, we calculate 4 key performances: 1. Limit of Detection (LOD) of each plate; 2. Intra-assay CV % of each plate, 3. Inter-assay CV % of each test day, and 4. Day-to-day CV %. For this example we prepared a total of 8 plates, each prepared at a different time using different batch of reagent. We perform the test on 2 different days and, for each day, we perform the tests on 4 different plates. On each plates, we perform the assay with 8 different concentration from 417 ppb, 213 ppb, 106 ppb, 53.4 ppb, 26.7 ppb, 13.3 ppb, 6.7 ppb and 0 ppb. For each concentration, we perform 6 replicates.

FIG. C8 shows the Lead in water test standard curve of individual R, G, B channel. RGB channel signals changes with $Pb^{2+}$ concentration Curve and converted to a single standard curve using a conversion equation Signal=−0.88*R+G−0.27*B+56.12. The converted data is fitted with 5PL logistic fitting. Error bar is Standard deviation of 6 replicate wells. The LOD, after conversion is 8.5 ppb.

FIG. C9 shows the sensitivity of all 8 different test plates in this example of the invention. Each test plate is prepared separately with different reagent and tested at different time. The average LOD achieved is 8 ppb, which is below the EPA action level at 15 ppb.

FIG. C10 Table of Intra-assay, Inter Assay and Day-to-day CV % of lead in water test. Near LOD, of each tests, the Intra-assay CV %~4%, the Inter-assay CV %~4% and the Day-to-day CV %~1.1%

In summary, this example shows a test of lead concentration in tap water that shows (1) Sensitivity: average LOD~8 ppb. All test plates show LOD that meets EPA standard (15 ppb), with the best LOD achieved is 3.9 ppb. (2) Repeatability: Intra-assay CV % at LOD 4%, Inter-assay CV % at LOD~4% and Day-to-day CV % at LOD~1.1%

D Foodstuff Safety and Allergen Test Using QMAX Device

Another aspect of the present invention provides devices and methods for safety and allergen test in foodstuff samples.

As summarized above, the devices, systems and methods in the present invention may find use in analyzing a foodstuff sample, e.g., a sample from raw food, processed food, cooked food, drinking water, etc., for the presence of foodstuff markers. A foodstuff marker may be any suitable marker, such as those shown in Table B9, below, that can be captured by a capturing agent that specifically binds the foodstuff marker in a CROF device configured with the capturing agent. The environmental sample may be obtained from any suitable source, such as tap water, drinking water, prepared food, processed food or raw food, etc. In some embodiments, the presence or absence, or the quantitative level of the foodstuff marker in the sample may be indicative of the safety or harmfulness to a subject if the food stuff is consumed. In some embodiments, the foodstuff marker is a substance derived from a pathogenic or microbial organism that is indicative of the presence of the organism in the foodstuff from which the sample was obtained. In some embodiments, the foodstuff marker is a toxic or harmful substance if consumed by a subject. In some embodiments, the foodstuff marker is a bioactive compound that may unintentionally or unexpectedly alter the physiology if consumed by the subject. In some embodiments, the foodstuff marker is indicative of the manner in which the foodstuff was obtained (grown, procured, caught, harvested, processed, cooked, etc.). In some embodiments, the foodstuff marker is indicative of the nutritional content of the foodstuff. In some embodiments, the foodstuff marker is an allergen that may induce an allergic reaction if the foodstuff from which the sample is obtained is consumed by a subject.

In some embodiments, the devices, systems and methods in the present invention further includes receiving or providing a report that indicates the safety or harmfulness for a subject to consume the food stuff from which the sample was obtained based on information including the measured level of the foodstuff marker. The information used to assess the safety of the foodstuff for consumption may include data other than the type and measured amount of the foodstuff marker. These other data may include any health condition associated with the consumer (allergies, pregnancy, chronic or acute diseases, current prescription medications, etc.).

The report may be generated by the device configured to read the CROF device, or may be generated at a remote location upon sending the data including the measured amount of the foodstuff marker. In some cases, a food safety expert may be at the remote location or have access to the data sent to the remote location, and may analyze or review the data to generate the report. The food safety expert may be a scientist or administrator at a governmental agency, such as the US Food and Drug Administration (FDA) or the CDC, a research institution, such as a university, or a private company. In certain embodiments, the food safety expert may send to the user instructions or recommendations based on the data transmitted by the device and/or analyzed at the remote location.

A list of foodstuff markers is available in Table D1. In some embodiments of the present invention, the QMAX device is used to detect the presence and/or quantity of analyte, including, but not limited to, the foodstuff markers listed in Table D1.

TABLE D1

| Foodstuff Markers | |
|---|---|
| Source/Class | Marker/target |
| Pathogens/microbes | *Bacillus anthracis* (LF), *Giardia lamblia, Legionella* , Total Coliforms (including fecal coliform and *E. Coli*), Viruses (enteric) *stapylococci* (e.g., *Staphylococcus epidermidis* and *Staphylococcus aureus* (enterotoxin A, B, C, G, I, cells, TSST-1), *Enterrococcus faecalis, Pseudomonas aeruginosa, Escherichia coli* (Shiga-like toxin, F4, F5, H, K, O, bacteriophage K1, K5, K13), other gram-positive bacteria, and gram-negative bacilli. *Clostridium difficile* (Toxin A, B), Bacteroidetes, *Cryptosporidium parvum* (GP900, p68 or cryptopain, oocyst), *Candida albicans, Bacillus anthracis, Bacillus stearothermophilus, Bacillus cereus, Bacillus licheniformis, Bacillus subtilis, Bacillus pumilus, Bacillus badius, Bacillus globigii, Salmonella typhimurium, Escherichia coli* O157:H7, Norovirus, *Listeria monocytogenes* (internalin), *Leptospira interrogans, Leptospira biflexa, Campylobacter jejuni, Campylobacter coli, Clostridium perfringens, Aspergillus flavus* (aflatoxins), *Aspergillus parasiticus*, (aflatoxins), Ebola virus (GP), *Histoplasma capsulatum Blastomyces dermatitidis* (A antigen), Gram-positive bacteria (teichoic acid), Gram-ngative bacteria (such as, *Pseudomonas aeruginosa, Klebsiella pneumoniae, Salmonella enteriditis, Enterobacter aerogenes, Enterobacter hermanii, Yersinia enterocolitica* and *Shigella sonnei*)(LPS), Polio virus, Influenza type A virus, Disease specific prion (PrP-d), Hepatitis A virus, *Toxoplasma gondii, Vibrio cholera, Vibrio parahaemolyticus, Vibrio vulnificus, Enterococcus faecalis, Enterococcus faecium, Angiostrongylus Cantonensis, Cyclospora cayetanensis, Entamoeba histolytica, Trichinella spiralis*, |
| Toxins/carcinogens | N-methylamino-L-alanine (BMAA), *Clostridium botulinum* neurotoxins, BoNT A, B, Ricin A, B; diphtheria toxin; Aristolochic acid; Colchicine, Ochratoxin A, Sterigmatocystin, Ergotamine, Fumonisins, Fusarin C, domoic acid, Brevetoxin, Mycotoxins, Antimony, Ciguatera fish poisoning, museinol, muscarine, psilocybin, *coprius artemetrais*, ibotenic acid, amanitin, Nitrite poisoning, Puffer fish (tetrodotoxin), histamine, amnesic, |
| Halogenated hydrocarbons | Heptachlor, chlordane |
| Heavy metals | Lead, mercury, cadmium, Chromium, Arsenic, Copper, Tin, Zinc, Thallium |
| Allergens | peanut (Ara h 1, Ara h 2, Ara h 6), fish, shellfish, mollusks, shrimp (*D. pteronyssinus* tropomyosin allergen, Der p 10) Cod (Gadc1); Atlantic salmon (Sals1); domestic cattle milk (Bosd4, Bosd5, Bosd6, Bosd7, Bosd8); chicken/egg (Gald1, Gald2, Gald3, Gald4, Gald5); shrimp (Mete1); shrimp (Pena1, Peni1); black tiger shrimp (Penm1, Penm2); squid (Todp1), brown garden snail (Helas1); abalone (Halm1); edible frog (Rane1, Rane2); oriental mustard (Braj1); rapeseed (Bran1); cabbage (Brao3); turnip (Brar1, Brar2); barley (Horv15, Horv16, Horv17, Horv21); rye (Secc20); wheat (Tria18, Tria19, Tria25, Tria26, gliadin); corn (Zeam14, Zeam25); rice (Orys1), celery (Apig1, Apig4, Apig5); carrot (Dauc1, Dauc4); hazelnut (Cora1.04, Cora2, Cora8); strawberry (Fraa1, Fraa3, Fraa4); apple (Mald1, Mald2, Mald3, Mald4); pear (Pyrc1, Pyrc4, Pyrc5); avocado (Persa1); apricot (Pruar1, Pruar3); sweet cherry (Pruav1, Pruav2, Pruav3, Pruav4); European plum (Prud3); almond (Prudu4); peach (Prup3, Prup4); asparagus (Aspao1); saffron crocus (Cros1, Cros2); lettuce (Lacs1); grape (Vitv1); banana (Musxp1); pineapple (Anac1, Anac2); lemon (Citl3); sweet orange (Cits1, Cits2, Cits3); litchi (Litc1); yellow mustard (Sina1); soybean (Glym1, Glym2, Glym3, Glym4); mung bean (Vigr1); peanut (Arah1, Arah2, Arah3, Arah4, Arah5, Arah6, Arah7, Arah8); lentil (Lenc1, Lenc2); pea (Piss1, Piss2); kiwi (Actc1, Actc2); bell pepper (Capa1w, Capa2); tomato (Lyce1, Lyce2, Lyce3); potato (Solat1, Solat2, Solat3, Solat4); Brazil nut (Bere1, Bere2); black walnut (Jugn1, Jugn2); English walnut (Jugr1, Jugr2, Jugr3); Cashew (Anao1, Anao2, Anao3); Castor bean (Ricc1); sesame (Sesi1, Sesi2, Sesi3, Sesi4, Sesi5, Sesi6); muskmelon (Cucm1, Cucm2, Cucm3); Chinese-date (Zizm1); *Anacardium occidentale* (Anao1.0101, Anao1.0102); *Apium graveolens* (Apig1.0101, Apig1.0201); *Daucus carota* (Dauc1.0101, Dauc1.0102, Dauc1.0103, Dauc1.0104, Dauc1.0105, Dauc1.0201); *Citrus sinensis* (Cits3.0101, Cits3.0102); *Glycine max* (Glym1.0101, Glym1.0102, Glym3.0101, Glym3.0102); *Lens culinaris* (Lenc1.0101, Lenc1.0102, Lenc1.0103); *Pisum sativum* (Piss1.0101, Piss1.0102); *Lycopersicon esculentum* (Lyce2.0101, Lyce2.0102); *Fragaria ananassa* (Fraa3.0101, Fraa3.0102, Fraa3.0201, Fraa3.0202, Fraa3.0203, Fraa3.0204, Fraa3.0301); *Malus domestica* (Mald1.0101, Mald1.0102, Mald1.0103, |

TABLE D1-continued

Foodstuff Markers

| Source/Class | Marker/target |
|---|---|
| | Mald1.0104, Mald1.0105, Mald1.0106, Mald1.0107, Mald1.0108, Mald1.0109, Mald1.0201, Mald1.0202, Mald1.0203, Mald1.0204, Mald1.0205, Mald1.0206, Mald1.0207, Mald1.0208, Mald1.0301, Mald1.0302, Mald1.0303, Mald1.0304, Mald1.0401, Mald1.0402, Mald1.0403, Mald3.0101w, Mald3.0102w, Mald3.0201w, Mald3.0202w, Mald3.0203w, Mald4.0101, Mald4.0102, Mald4.0201, Mald4.0202, Mald4.0301, Mald4.0302); *Prunus avium* (Pruav1.0101, Pruav1.0201, Pruav1.0202, Pruav1.0203); and *Prunus persica* (Prup4.0101, Prup4.0201) |
| Synthetic hormone analogues | 17beta-estradiol (E2), estrone (EI), estrogen (ES: EI + E2 + estradiol (E3)), 1 7alfa-ethynylestradiol (EE2), 4-nonylphenpol, testosterone, Diethylstilbestrol (DES), recombinant bovine growth hormone (rBGH) |
| Pesticides | Dieldrin, carbaryl, chlorpyrifos, parathion, aldrin, endosulfan I, endrin, toxaphene, O-ethyl O-4-nitrophenyl phenylphosphono-thioate (EPN), fenitrothion, pirimiphos-methyl, thiabendazole, methiocarb, Carbendazim, deltamethrin, Avermectin, Carbaryl, Cyanazine, Kresoxim, resmethrin, kadethrin, cyhalothrin, biphenthrin, fenpropathrin, allethrin and tralomethrin; aromatic-substituted alkanecarboxylic acid esters such as fenvarerate, flucythrinate, fluvalinate and cycloprothrin; and non-ester compounds such as etofenprox, halfenprox (MTI-732), 1-(3-phenoxyphenyl)-4-(4-ethoxyphenyl)-4-methylpentane (MTI-790), 1-(3-phenoxy-4-fluorophenyl)-4-(4-ethoxyphenyl)-4-methylpentane (MTI-800), dimethyl-(4-ethoxyphenyl)-(3-phenoxybenzyloxy)silane (SSI-116), silafluofen and PP-682, carbofuran, triazophos |
| Herbicide | atrazine, deethylatrazine, cyanazine, terbuthylazine, terbutryn, molinate, simazine, prometon, promteryn, hydroxyatrazine, 2,6-dichlorobenzamide (BAM), N-dealkylated triazines, mecoprop, thiram, acetochlor, alachlor, Chlorothalonil, Chlorsulfuron, Fenoxaprop ethyl, Linuron, monuron, diuron, Quizalofop-ethyl, Imazalil, Iprodione, Iprovalicarb, Myclobutanil |
| Industrial material/waste | Dioxin (2,3,7,8-TCDD), 4-tert-octylphenol, bisphenol A (BPA), Styrene, Di(2-ethylhexyl) phthalate, Dibutyl phthalate (DBP), benzophenone, benzene, trichloroethylene, polychlorinated biphenyl (PCB), nonylphenol, p-cresol, melamine, xylene, Sodium Fluoride |
| Antibiotics | 3-Amino-5-morpholinomethyl-2-oxazolidone (AMOZ; tissue bound metabolite of furaltadone), oxytetracycline, rolitetracycline, Actinomycin D, Amikacin sulfate, Aminoglycosides, nitrofuran (AOZ), Chloramphenicol, Doxycycline, Streptomycin, gentamicin, neomycin, kanamycin, sulfamethazine, enrofloxacin, sulfadiazine, enrofloxacin |
| Food coloring/ additive/ preservative | Tartrazine, ethoxyquin, erythritol, penicillin, Fluoroquinolone, Malachite Green/Leucomalachite Green, C.I. Solvent Yellow 14 (Sudan I), |
| Food preparation | Acrylamide, 2-amino-3-methylimidazo(4,5-f)quinolone, Benzo[a]pyrene |
| Nutritional content | Vitamins A (retinol), B12 (cobalmins), B6 (pyridoxine), B1 (thiamin), B2 (riboflavin), B3 (niacin), B5 (D-pantothenic acid), B7 (biotin), B9 (folic acid), C, D, E (alpha-tocopherol); |
| Other | Caffeine, Ovine myofibril proteins, Etodolac |

E. Uniform Sample Thickness Pressed by an Imprecise Force.

In some embodiments of devices or methods of forming uniform sample thickness by pressing with an imprecise force described herein and in the provisional 62/456,504, filed on Feb. 8, 2017., which is incorporated herein in the its entirety for all purposes.

In some embodiments, the imprecise force is around 0.01 kg, 0.05 kg, 0.1 kg, 0.25 kg, 0.5 kg, 1 kg, 2.5 kg, 5 kg, 7.5 kg, 10 kg, 20 kg, 25 kg, 30 kg, 40 kg, 50 kg, 60 kg, 70 kg, 80 kg, 100 kg, 200 kg, or in a range between any two of these values; and a preferred range of 0.5-2 kg, 2-5 kg, 5-7.5 kg, 7.5-10 kg, 10-20 kg, 20-40 kg, 40-60 kg, or 60-100 kg.

In some embodiments, the imprecise force is applied by human hand, for example, e.g., by pinching an object together between a thumb and index finger, or by pinching and rubbing an object together between a thumb and index finger.

In some embodiments, the hand pressing force is around 0.05 kg, 0.1 kg, 0.25 kg, 0.5 kg, 1 kg, 2.5 kg, 5 kg, 7.5 kg, 10 kg, 20 kg, 25 kg, 30 kg, 40 kg, 50 kg, 60 kg, or in a range between any two of these values; and a preferred range of 0.5-1 kg, 1-2 kg, 2-4 kg, 4-6 kg, 6-10 kg, 10-20 kg, 20-40 kg, or 40-60 kg.

In some embodiments, the hand pressing has a pressure of 0.01 $kg/cm^2$, 0.1 $kg/cm^2$, 0.5 $kg/cm^2$, 1 $kg/cm^2$, 2 $kg/cm^2$, 2.5 $kg/cm^2$, 5 $kg/cm^2$, 10 $kg/cm^2$, 20 $kg/cm^2$, 30 $kg/cm^2$, 40 $kg/cm^2$, 50 $kg/cm^2$, 60 $kg/cm^2$, 100 $kg/cm^2$, 150 $kg/cm^2$, 200 $kg/cm^2$, or a range between any two of the values; and a preferred range of 0.1 $kg/cm^2$ to 0.5 $kg/cm^2$, 0.5 $kg/cm^2$ to 1 $kg/cm^2$, 1 $kg/cm^2$ to 5 $kg/cm^2$, or 5 $kg/cm^2$ to 10 $kg/cm^2$.

As used herein, the term "imprecise" in the context of a force (e.g. "imprecise pressing force") refers to a force that (a) has a magnitude that is not precisely known or precisely predictable at the time the force is applied;

(b) varies in magnitude from one application of the force to the next; and (c) the imprecision (i.e. the variation) of the force in (a) and (c) is at least 20% of the total force that actually is applied.

An imprecise force can be applied by human hand, for example, e.g., by pinching an object together between a thumb and index finger, or by pinching and rubbing an object together between a thumb and index finger.

EA. Imprecise Force, Specify IGS^4/hE

EA1. A device for forming a thin fluidic sample layer with a uniform predetermined thickness by pressing with an imprecise pressing force, comprising:
  a first plate, a second plate, and spacers, wherein:
  i. the plates are movable relative to each other into different configurations;
  ii. one or both plates are flexible;
  iii. each of the plates comprises an inner surface that has a sample contact area for contacting a fluidic sample;
  iv. each of the plates comprises, on its respective outer surface, a force area for applying an imprecise pressing force that forces the plates together;
  v. one or both of the plates comprise the spacers that are permanently fixed on the inner surface of a respective plate;
  vi. the spacers have a predetermined substantially uniform height that is equal to or less than 200 microns, and a predetermined fixed inter-spacer-distance;
  vii. the fourth power of the inter-spacer-distance (IDS) divided by the thickness (h) and the Young's modulus (E) of the flexible plate ($ISD^4/(hE)$) is $5 \times 10^6$ $um^3$/GPa or less; and
  viii. at least one of the spacers is inside the sample contact area;
  wherein one of the configurations is an open configuration, in which: the two plates are partially or completely separated apart, the spacing between the plates is not regulated by the spacers, and the sample is deposited on one or both of the plates;
  wherein another of the configurations is a closed configuration which is configured after the sample is deposited in the open configuration and the plates are forced to the closed configuration by applying the imprecise pressing force on the force area; and in the closed configuration: at least part of the sample is compressed by the two plates into a layer of highly uniform thickness and is substantially stagnant relative to the plates, wherein the uniform thickness of the layer is confined by the sample contact areas of the two plates and is regulated by the plates and the spacers.

EA2. A method of forming a thin fluidic sample layer with a uniform predetermined thickness by pressing with an imprecise pressing force, comprising the steps of:
  (a) obtaining a first plate, a second plate, and spacers, wherein:
    i. the plates are movable relative to each other into different configurations;
    ii. one or both plates are flexible;
    iii. each of the plates comprises an inner surface that has a sample contact area for contacting a fluidic sample;
    iv. each of the plates comprises, on its respective outer surface, a force area for applying an imprecise pressing force that forces the plates together;
    v. one or both of the plates comprise the spacers that are permanently fixed on the inner surface of a respective plate;
    vi. the spacers have a predetermined substantially uniform height that is equal to or less than 200 microns, and a predetermined fixed inter-spacer-distance;
    vii. the fourth power of the inter-spacer-distance (IDS) divided by the thickness (h) and the Young's modulus (E) of the flexible plate ($ISD^4/(hE)$) is $5 \times 10^6$ $um^3$/GPa or less; and
    viii. at least one of the spacers is inside the sample contact area;
  (b) obtaining a fluidic sample;
  (c) depositing the sample on one or both of the plates; when the plates are configured in an open configuration, wherein the open configuration is a configuration in which the two plates are partially or completely separated apart and the spacing between the plates is not regulated by the spacers;
  (d) after (c), using the two plates to compress at least part of the sample into a layer of substantially uniform thickness that is confined by the sample contact surfaces of the plates, wherein the uniform thickness of the layer is regulated by the spacers and the plates, wherein the compressing comprises:
    bringing the two plates together; and
    conformable pressing, either in parallel or sequentially, an area of at least one of the plates to press the plates together to a closed configuration, wherein the conformable pressing generates a substantially uniform pressure on the plates over the at least part of the sample, and the pressing spreads the at least part of the sample laterally between the sample contact surfaces of the plates, and wherein the closed configuration is a configuration in which the spacing between the plates in the layer of uniform thickness region is regulated by the spacers; and wherein the reduced thickness of the sample reduces the time for mixing the reagents on the storage site with the sample, and
    wherein the force that presses the two plates into the closed configuration is an imprecise pressing force provided by human hand.

EB. Hand pressing, Specify Spacer Hardness-Contact Area Product

EB1. A device for forming a thin fluidic sample layer with a uniform predetermined thickness by pressing with an imprecise force, comprising:
  a first plate, a second plate, and spacers, wherein:
  i. the plates are movable relative to each other into different configurations;
  ii. one or both plates are flexible;
  iii. each of the plates comprises, on its respective inner surface, a sample contact area for contacting and/or compressing a fluidic sample;
  iv. each of the plates comprises, on its respective outer surface, an area for applying a force that forces the plates together;
  v. one or both of the plates comprise the spacers that are permanently fixed on the inner surface of a respective plate;
  vi. the spacers have a predetermined substantially uniform height that is equal to or less than 200 microns, a predetermined width, and a predetermined inter-spacer-distance;
  vii. a ratio of the inter-spacer-distance to the spacer width is 1.5 or larger; and
  viii. at least one of the spacers is inside the sample contact area;

wherein one of the configurations is an open configuration, in which: the two plates are partially or completely separated apart, the spacing between the plates is not regulated by the spacers, and the sample is deposited on one or both of the plates;

wherein another of the configurations is a closed configuration which is configured after the sample deposition in the open configuration; and in the closed configuration: at least part of the sample is compressed by the two plates into a layer of highly uniform thickness and is substantially stagnant relative to the plates, wherein the uniform thickness of the layer is confined by the sample contact areas of the two plates and is regulated by the plates and the spacers; and wherein the force that presses the two plates into the closed configuration is an imprecise pressing force provided by human hand.

EB2. A method of forming a thin fluidic sample layer with a uniform predetermined thickness by pressing with an imprecise pressing force, comprising the steps of:
(a) obtaining a first plate, a second plate, and spacers, wherein:
  i. the plates are movable relative to each other into different configurations;
  ii. one or both plates are flexible;
  iii. each of the plates comprises, on its respective inner surface, a sample contact area for contacting and/or compressing a fluidic sample;
  iv. each of the plates comprises, on its respective outer surface, an area for applying a force that forces the plates together;
  v. one or both of the plates comprise the spacers that are permanently fixed on the inner surface of a respective plate;
  vi. the spacers have a predetermined substantially uniform height that is equal to or less than 200 microns, a predetermined width, and a predetermined inter-spacer-distance;
  vii. a ratio of the inter-spacer-distance to the spacer width is 1.5 or larger; and
  viii. at least one of the spacers is inside the sample contact area;
(b) obtaining a fluidic sample;
(c) depositing the sample on one or both of the plates; when the plates are configured in an open configuration, wherein the open configuration is a configuration in which the two plates are partially or completely separated apart and the spacing between the plates is not regulated by the spacers;
(d) after (c), using the two plates to compress at least part of the sample into a layer of substantially uniform thickness that is confined by the sample contact surfaces of the plates, wherein the uniform thickness of the layer is regulated by the spacers and the plates, wherein the compressing comprises:
  bringing the two plates together; and
  conformable pressing, either in parallel or sequentially, an area of at least one of the plates to press the plates together to a closed configuration, wherein the conformable pressing generates a substantially uniform pressure on the plates over the at least part of the sample, and the pressing spreads the at least part of the sample laterally between the sample contact surfaces of the plates, and wherein the closed configuration is a configuration in which the spacing between the plates in the layer of uniform thickness region is regulated by the spacers; and wherein the reduced thickness of the sample reduces the time for mixing the reagents on the storage site with the sample, and wherein the force that presses the two plates into the closed configuration is an imprecise pressing force provided by human hand.

EC. Hand Pressing, Specify IDS/hE & Spacer Hardness-Contact Area Product

EC1. A device for forming a thin fluidic sample layer with a uniform predetermined thickness by pressing with an imprecise force, comprising:
a first plate, a second plate, and spacers, wherein:
  i. the plates are movable relative to each other into different configurations;
  ii. one or both plates are flexible;
  iii. each of the plates comprises, on its respective inner surface, a sample contact area for contacting and/or compressing a fluidic sample;
  iv. each of the plates comprises, on its respective outer surface, an area for applying a force that forces the plates together;
  v. one or both of the plates comprise the spacers that are permanently fixed on the inner surface of a respective plate;
  vi. the spacers have a predetermined substantially uniform height that is equal to or less than 200 microns, a predetermined width, and a predetermined inter-spacer-distance;
  vii. a ratio of the inter-spacer-distance to the spacer width is 1.5 or larger; and
  viii. at least one of the spacers is inside the sample contact area;

wherein one of the configurations is an open configuration, in which: the two plates are partially or completely separated apart, the spacing between the plates is not regulated by the spacers, and the sample is deposited on one or both of the plates;

wherein another of the configurations is a closed configuration which is configured after the sample deposition in the open configuration; and in the closed configuration: at least part of the sample is compressed by the two plates into a layer of highly uniform thickness and is substantially stagnant relative to the plates, wherein the uniform thickness of the layer is confined by the sample contact areas of the two plates and is regulated by the plates and the spacers;

wherein the force that presses the two plates into the closed configuration is imprecise, and is provided by human hand.

EC2. A method of forming a thin fluidic sample layer with a uniform predetermined thickness by pressing with an imprecise pressing force, comprising the steps of:
(a) obtaining a first plate, a second plate, and spacers, wherein:
  i. the plates are movable relative to each other into different configurations;
  ii. one or both plates are flexible;
  iii. each of the plates comprises, on its respective inner surface, a sample contact area for contacting and/or compressing a fluidic sample;
  iv. each of the plates comprises, on its respective outer surface, an area for applying a force that forces the plates together;
  v. one or both of the plates comprise the spacers that are permanently fixed on the inner surface of a respective plate;

vi. the spacers have a predetermined substantially uniform height that is equal to or less than 200 microns, a predetermined width, and a predetermined inter-spacer-distance;
vii. a ratio of the inter-spacer-distance to the spacer width is 1.5 or larger; and
viii. at least one of the spacers is inside the sample contact area;
(b) obtaining a fluidic sample;
(c) depositing the sample on one or both of the plates; when the plates are configured in an open configuration, wherein the open configuration is a configuration in which the two plates are partially or completely separated apart and the spacing between the plates is not regulated by the spacers;
(d) after (c), using the two plates to compress at least part of the sample into a layer of substantially uniform thickness that is confined by the sample contact surfaces of the plates, wherein the uniform thickness of the layer is regulated by the spacers and the plates, wherein the compressing comprises:
bringing the two plates together; and
conformable pressing, either in parallel or sequentially, an area of at least one of the plates to press the plates together to a closed configuration, wherein the conformable pressing generates a substantially uniform pressure on the plates over the at least part of the sample, and the pressing spreads the at least part of the sample laterally between the sample contact surfaces of the plates, and wherein the closed configuration is a configuration in which the spacing between the plates in the layer of uniform thickness region is regulated by the spacers; and wherein the reduced thickness of the sample reduces the time for mixing the reagents on the storage site with the sample, and
wherein the force that presses the two plates into the closed configuration is an imprecise pressing force provided by human hand.

ED. Hand Pressing, Specify Pillar Spacer and Ratio of IDS/W

ED 1. A device for forming a thin fluidic sample layer with a uniform predetermined thickness by pressing with an imprecise force, comprising:
a first plate, a second plate, and spacers, wherein:
i. the plates are movable relative to each other into different configurations;
ii. one or both plates are flexible;
iii. each of the plates comprises, on its respective inner surface, a sample contact area for contacting and/or compressing a fluidic sample;
iv. each of the plates comprises, on its respective outer surface, an area for applying a force that forces the plates together;
v. one or both of the plates comprise the spacers that are permanently fixed on the inner surface of a respective plate;
vi. the spacers have a predetermined substantially uniform height that is equal to or less than 200 microns, a predetermined width, and a predetermined inter-spacer-distance;
vii. a ratio of the inter-spacer-distance to the spacer width is 1.5 or larger.
viii. at least one of the spacers is inside the sample contact area; and
wherein one of the configurations is an open configuration, in which: the two plates are partially or completely separated apart, the spacing between the plates is not regulated by the spacers, and the sample is deposited on one or both of the plates;
wherein another of the configurations is a closed configuration which is configured after the sample deposition in the open configuration; and in the closed configuration: at least part of the sample is compressed by the two plates into a layer of highly uniform thickness and is substantially stagnant relative to the plates, wherein the uniform thickness of the layer is confined by the sample contact areas of the two plates and is regulated by the plates and the spacers;
wherein the force that presses the two plates into the closed configuration is imprecise, and is provided by human hand.

ED2. A method of forming a thin fluidic sample layer with a uniform predetermined thickness by pressing with an imprecise pressing force, comprising the steps of:
(a) obtaining a first plate, a second plate, and spacers, wherein:
i. the plates are movable relative to each other into different configurations;
ii. one or both plates are flexible;
iii. each of the plates comprises, on its respective inner surface, a sample contact area for contacting and/or compressing a fluidic sample;
iv. each of the plates comprises, on its respective outer surface, an area for applying a force that forces the plates together;
v. one or both of the plates comprise the spacers that are permanently fixed on the inner surface of a respective plate;
vi. the spacers have a predetermined substantially uniform height that is equal to or less than 200 microns, a predetermined width, and a predetermined inter-spacer-distance;
vii. a ratio of the inter-spacer-distance to the spacer width is 1.5 or larger.
viii. at least one of the spacers is inside the sample contact area; and
(b) obtaining a fluidic sample;
(c) depositing the sample on one or both of the plates; when the plates are configured in an open configuration, wherein the open configuration is a configuration in which the two plates are partially or completely separated apart and the spacing between the plates is not regulated by the spacers;
(d) after (c), using the two plates to compress at least part of the sample into a layer of substantially uniform thickness that is confined by the sample contact surfaces of the plates, wherein the uniform thickness of the layer is regulated by the spacers and the plates, wherein the compressing comprises:
bringing the two plates together; and
conformable pressing, either in parallel or sequentially, an area of at least one of the plates to press the plates together to a closed configuration, wherein the conformable pressing generates a substantially uniform pressure on the plates over the at least part of the sample, and the pressing spreads the at least part of the sample laterally between the sample contact surfaces of the plates, and wherein the closed configuration is a configuration in which the spacing between the plates in the layer of uniform thickness region is regulated by the spacers; and wherein the reduced thickness of the sample reduces the time for mixing the reagents on the storage site with the sample, and wherein the force that presses the two plates into the closed configuration is an imprecise pressing force provided by human hand.

EE. Volume Determination, Specify IGS^4/hE

EE1. A device for determining a relevant sample volume by pressing with an imprecise force provided by human hand, comprising:

a first plate, a second plate, spacers, and an area-determination device, wherein:
i. the plates are movable relative to each other into different configurations;
ii. one or both plates are flexible;
iii. each of the plates comprises, on its respective inner surface, a sample contact area for contacting and/or compressing a fluidic sample that has a relevant volume to be measured;
iv. each of the plates comprises, on its respective outer surface, an area for applying a force that forces the plates together;
v. one or both of the plates comprise the spacers that are permanently fixed on the inner surface of a respective plate;
vi. the spacers have a predetermined substantially uniform height that is equal to or less than 200 microns, and a predetermined constant inter-spacer-distance;
vii. a fourth power of the inter-spacer-distance (IDS) divided by the thickness (h) and the Young's modulus (E) of the flexible plate ($ISD^4/(hE)$) is $5 \times 10^6$ um$^3$/GPa or less.
viii. at least one of the spacers is inside the sample contact area; and
ix. the area-determination device is configured to determine the lateral area of the relevant volume;

wherein one of the configurations is an open configuration, in which: the two plates are partially or completely separated apart, the spacing between the plates is not regulated by the spacers, and the sample is deposited on one or both of the plates;

wherein another of the configurations is a closed configuration which is configured after the sample deposition in the open configuration; and in the closed configuration: at least part of the sample is compressed by the two plates into a layer of highly uniform thickness and is substantially stagnant relative to the plates, wherein the uniform thickness of the layer is confined by the sample contact areas of the two plates and is regulated by the plates and the spacers;

wherein the relevant volume of the sample is a partial or entire volume of the uniform thickness layer and the value of the relevant volume is determined by the uniform thickness and the determined lateral area; and wherein the force that presses the two plates into the closed configuration is imprecise, and is provided by human hand.

The device of any prior embodiment, wherein the area-determination device is a camera.

The area-determination device comprises an area in the sample contact area of a plate, wherein the area is less than 1/100, 1/20, 1/10, 1/6, 1/5, 1/4, 1/3, 1/2, 2/3 of the sample contact area, or in a range between any of the two values.

The area-determination device comprises a camera and an area in the sample contact area of a plate, wherein the area is in contact with the sample.

EE2. A method of forming a thin fluidic sample layer with a uniform predetermined thickness by pressing with an imprecise pressing force, comprising the steps of:
(a) obtaining a first plate, a second plate, and spacers, wherein:
i. the plates are movable relative to each other into different configurations;
ii. one or both plates are flexible;
iii. each of the plates comprises, on its respective inner surface, a sample contact area for contacting and/or compressing a fluidic sample that has a relevant volume to be measured;
iv. each of the plates comprises, on its respective outer surface, an area for applying a force that forces the plates together;
v. one or both of the plates comprise the spacers that are permanently fixed on the inner surface of a respective plate;
vi. the spacers have a predetermined substantially uniform height that is equal to or less than 200 microns, and a predetermined constant inter-spacer-distance;
vii. a fourth power of the inter-spacer-distance (IDS) divided by the thickness (h) and the Young's modulus (E) of the flexible plate ($ISD^4/(hE)$) is $5 \times 10^6$ um$^3$/GPa or less.
viii. at least one of the spacers is inside the sample contact area; and
ix. the area-determination device is configured to determine the lateral area of the relevant volume;
(b) obtaining a fluidic sample;
(c) depositing the sample on one or both of the plates; when the plates are configured in an open configuration, wherein the open configuration is a configuration in which the two plates are partially or completely separated apart and the spacing between the plates is not regulated by the spacers;
(d) after (c), using the two plates to compress at least part of the sample into a layer of substantially uniform thickness that is confined by the sample contact surfaces of the plates, wherein the uniform thickness of the layer is regulated by the spacers and the plates, wherein the compressing comprises:
bringing the two plates together; and
conformable pressing, either in parallel or sequentially, an area of at least one of the plates to press the plates together to a closed configuration, wherein the conformable pressing generates a substantially uniform pressure on the plates over the at least part of the sample, and the pressing spreads the at least part of the sample laterally between the sample contact surfaces of the plates, and wherein the closed configuration is a configuration in which the spacing between the plates in the layer of uniform thickness region is regulated by the spacers; and wherein the reduced thickness of the sample reduces the time for mixing the reagents on the storage site with the sample, and
wherein the force that presses the two plates into the closed configuration is an imprecise pressing force provided by human hand.

EF. Volume Determination, Specify IGS^4/hE

EF1. A device for determining a relevant sample volume by pressing with an imprecise force provided by human hand, comprising:

a first plate, a second plate, spacers, and area-determination device, wherein:
i. the plates are movable relative to each other into different configurations;
ii. one or both plates are flexible;

iii. each of the plates comprises, on its respective inner surface, a sample contact area for contacting and/or compressing a fluidic sample that has a relevant volume to be measured;
iv. each of the plates comprises, on its respective outer surface, an area for applying a force that forces the plates together;
v. one or both of the plates comprise the spacers that are permanently fixed on the inner surface of a respective plate;
vi. the spacers have a predetermined substantially uniform height that is equal to or less than 200 microns, and a predetermined constant inter-spacer-distance;
vii. a fourth power of the inter-spacer-distance (IDS) divided by the thickness (h) and the Young's modulus (E) of the flexible plate (ISD$^4$/(hE)) is $5\times10^6$ um$^3$/GPa or less.
viii. at least one of the spacers is inside the sample contact area; and
ix. the area-determination device is configured to determine the lateral area of the relevant volume;
wherein one of the configurations is an open configuration, in which: the two plates are partially or completely separated apart, the spacing between the plates is not regulated by the spacers, and the sample is deposited on one or both of the plates;
wherein another of the configurations is a closed configuration which is configured after the sample deposition in the open configuration; and in the closed configuration: at least part of the sample is compressed by the two plates into a layer of highly uniform thickness and is substantially stagnant relative to the plates, wherein the uniform thickness of the layer is confined by the sample contact areas of the two plates and is regulated by the plates and the spacers;
wherein the relevant volume of the sample is a partial or entire volume of the uniform thickness layer and the value of the relevant volume is determined by the uniform thickness and the determined lateral area; and
wherein the force that presses the two plates into the closed configuration is imprecise, and is provided by human hand.

EF2. A method of forming a thin fluidic sample layer with a uniform predetermined thickness by pressing with an imprecise pressing force, comprising the steps of:
(a) obtaining a first plate, a second plate, and spacers, wherein:
  i. the plates are movable relative to each other into different configurations;
  ii. one or both plates are flexible;
  iii. each of the plates comprises, on its respective inner surface, a sample contact area for contacting and/or compressing a fluidic sample that has a relevant volume to be measured;
  iv. each of the plates comprises, on its respective outer surface, an area for applying a force that forces the plates together;
  v. one or both of the plates comprise the spacers that are permanently fixed on the inner surface of a respective plate;
  vi. the spacers have a predetermined substantially uniform height that is equal to or less than 200 microns, and a predetermined constant inter-spacer-distance;
  vii. a fourth power of the inter-spacer-distance (IDS) divided by the thickness (h) and the Young's modulus (E) of the flexible plate (ISD$^4$/(hE)) is $5\times10^6$ um$^3$/GPa or less.
  viii. at least one of the spacers is inside the sample contact area; and
  ix. the area-determination device is configured to determine the lateral area of the relevant volume;
(b) obtaining a fluidic sample;
(c) depositing the sample on one or both of the plates; when the plates are configured in an open configuration, wherein the open configuration is a configuration in which the two plates are partially or completely separated apart and the spacing between the plates is not regulated by the spacers;
(d) after (c), using the two plates to compress at least part of the sample into a layer of substantially uniform thickness that is confined by the sample contact surfaces of the plates, wherein the uniform thickness of the layer is regulated by the spacers and the plates, wherein the compressing comprises:
  bringing the two plates together; and
  conformable pressing, either in parallel or sequentially, an area of at least one of the plates to press the plates together to a closed configuration, wherein the conformable pressing generates a substantially uniform pressure on the plates over the at least part of the sample, and the pressing spreads the at least part of the sample laterally between the sample contact surfaces of the plates, and wherein the closed configuration is a configuration in which the spacing between the plates in the layer of uniform thickness region is regulated by the spacers; and wherein the reduced thickness of the sample reduces the time for mixing the reagents on the storage site with the sample, and
  wherein the force that presses the two plates into the closed configuration is an imprecise pressing force provided by human hand.

EG. More Embodiments

The term "imprecise force" refers to a force that has a magnitude that is completely unknown, known only in a magnitude range but not in a particular magnitude value (the magnitude range varies at least 20% from the minimum to the maximum of the range), or unpredictable at the time that a force is applied. Examples of an imprecise force include that the magnitude of an imprecise force may vary from one application of the force to the next, may be uneven across the area upon which the force is applied, and may vary over the time that the force is being applied. An imprecise force does not need to be measured at the time that it is applied.

The devices or methods of any prior embodiment, wherein the deformable sample is a fluidic sample.

The devices or methods of any prior embodiment, wherein the deformable sample is a liquid sample.

The devices or methods of any prior embodiment, wherein the imprecision force has a variation at least 30% of the total force that actually is applied.

The devices or methods of any prior embodiment, wherein the imprecision force has a variation at least 20%, 30%, 40%, 50%, 60, 70%, 80%, 90% 100%, 150%, 200%, 300%, 500%, or in a range of any two values, of the total force that actually is applied.

1. The device of any prior embodiment, wherein spacers have a flat top.
2. The device of any prior embodiment, wherein the device is further configured to have, after the pressing force is removed, a sample thickness that is substantially the same in thickness and uniformity as that when the force is applied.

3. The device of any prior embodiment, wherein the imprecise force is provided by human hand.
4. The device of any prior embodiment, wherein the inter spacer distance is substantially constant.
5. The device of any prior embodiment, wherein the inter spacer distance is substantially periodic in the area of the uniform sample thickness area.
6. The device of any prior embodiment, wherein the multiplication product of the filling factor and the Young's modulus of the spacer is 2 MPa or larger.
7. The device of any prior embodiment, wherein the force is applied by hand directly or indirectly.
8. The device of any prior embodiment, wherein the force applied is in the range of 5 N to 20 N.
9. The device of any prior embodiment wherein the highly uniform layer has a thickness that varies by less than 15%, 10%, or 5% of an average thickness.
10. The device of any prior embodiment, wherein the imprecise force is applied by pinching the device between a thumb and forefinger.
11. The device of any prior embodiment, wherein the predetermined sample thickness is larger than the spacer height.
12. The device of any prior embodiment, wherein the device holds itself in the closed configuration after the pressing force has been removed.
13. The device of any prior embodiment, wherein the uniform thickness sample layer area is larger than that area upon which the pressing force is applied.
14. The device of any prior embodiment, wherein the spacers do not significantly deform during application of the pressing force.
15. The device of any prior embodiment, wherein the pressing force is not predetermined beforehand and is not measured.

F. Binding Site and Storage Site on the Same Plate

Another aspect of the present invention provides devices and methods for bio/chemical assays using QMAX device in which binding site and storage site are on the same plate, meaning both capture agent and second agent are coated on the same plate.

FA1. A method for assaying a sample, comprising
(a) obtaining a first plate comprising, on its inner surface, a sample contact area for contacting a sample that contains a target analyte;
(b) obtaining a second plate comprising a sample contact area that comprises an assaying area, wherein the assaying area comprises
  (i) an immobilized capture agent that binds a target analyte in a sample, and
  (ii) a second agent that is capable of, upon contacting the sample, diffusing in the sample;
  wherein the first plate and second plate are movable relative to each other into different configurations, including an open and a closed configurations;
(c) depositing, in the open configuration, the sample on one or both of the sample contact areas of the plates, wherein in the open configuration, the sample contact areas of the plates are separated larger than 200 um;
(d) after (c), bringing the two plates to a closed configuration, wherein, in the closed configuration, at least part of the sample deposited in (c) is confined between the sample contact areas of the two plates, and has an average thickness in the range of 0.01 to 200 μm; and
(e) detecting a signal related to an analyte that is captured by the binding site.

FB1. A device for performing a competitive assay, comprising:
a first plate comprising, on its inner surface, a sample contact area for contacting a sample that contains a target analyte;
a second plate comprising a sample contact area that comprises an assaying area,
  wherein the assaying area comprises
  (i) an immobilized capture agent that binds a target analyte in a sample, and
  (ii) a second agent that is capable of, upon contacting the sample, diffusing in the sample;
  wherein the first plate and second plate are movable relative to each other into different configurations;
  wherein one of the configurations is an open configuration, in which the plates are partially or entirely separated apart, and the average spacing between the sample contact areas of the plates is larger than 300 um; and
  wherein another configuration is a closed configuration in which the average spacing between the sample contact areas of the plates is 200 μm or less.

The method or device of any prior embodiment, wherein the capture agents and the second agents are separated by a distance that is at least 2 times less than the average spacing between the sample contact area of the two plates.

The method or device of any prior embodiment, wherein the capture agents and the second agents are separated by a distance that is at least 2 times, 3 times, 5 times, 10 times, 20 times, 30 times, 50 times, 100 times, 200 times,300 times,500 times, 1000 times, 2000 times, 5000 times, 10000 times, 5000 times, less than the average spacing between the sample contact area of the two plates, or in a range of any two values.

The method or device of any prior embodiment, wherein the signal related to the analyte captured by the capture agent are the signals coming from (i) the analyte captured by the capture agent, (ii) the label attached an analyte that is captured by the binding site, or (iii) both (i) and (ii).

The method or device of any prior embodiment, wherein one or both of the sample contact areas comprise spacers, wherein the spacers regulate the spacing between the sample contact areas of the plates when the plates are in the closed configuration.

The method of any prior embodiment, wherein the spacing between the sample contact areas when the plates are in a closed configuration is regulated by spacers.

The device of any prior embodiment, wherein the device further comprises spacers that regulate the spacing between the sample contact areas when the plates are in a closed configuration.

The method or device of any prior embodiment, wherein the storage site further comprises another reagent.

The method or device of any prior embodiment, wherein the binding site comprises, in addition to immobilized capture agent, another reagent that is, upon contacting the sample, capable of diffusion in the sample, The method or device of any prior embodiment, wherein the detection of the signal is electrical, optical, or both. (Will add more on the detection later. Fluorescence, SPR, etc.).

The method or device of any prior embodiment, wherein the sample is a blood sample (whole blood, plasma, or serum).

The method or device of any prior embodiment, wherein the material of fluorescent microsphere is dielectric, (e.g. $SiO_2$, Polystyrene,) or the combination of dielectric materials thereof.

The method or device of any prior embodiment, which comprises steps of adding the detection agent of said fluorescence label to the first plate to bind competitive agent.

The method or device of any prior embodiment, which comprises steps of washing after the detection agent is added.

The embodiments in these applications herein incorporated can be regarded in combination with one another or as a single invention, rather than as discrete and independent filings.

Moreover, the exemplary assay recipes disclosed herein are applicable to embodiments including but not limited to: bio/chemical assays, QMAX cards and systems, QMAX with hinges, notches, recessed edges and sliders, assays and devices with uniform sample thickness, smartphone detection systems, cloud computing designs, various detection methods, labels, capture agents and detection agents, analytes, diseases, applications, and samples; the various embodiments are disclosed, described, and/or referred to in the aforementioned applications, all of which are hereby incorporated in reference by their entireties.

Other Embodiments

The present invention includes a variety of embodiments, which can be combined in multiple ways as long as the various components do not contradict one another. The embodiments should be regarded as a single invention file: each filing has other filing as the references and is also referenced in its entirety and for all purpose, rather than as a discrete independent. These embodiments include not only the disclosures in the current file, but also the documents that are herein referenced, incorporated, or to which priority is claimed.

(1) Definitions

The terms used in describing the devices, systems, and methods herein disclosed are defined in the current application, or in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

The terms "CROF Card (or card)", "COF Card", "QMAX-Card", "Q-Card", "CROF device", "COF device", "QMAX-device", "CROF plates", "COF plates", and "QMAX-plates" are interchangeable, except that in some embodiments, the COF card does not comprise spacers; and the terms refer to a device that comprises a first plate and a second plate that are movable relative to each other into different configurations (including an open configuration and a closed configuration), and that comprises spacers (except some embodiments of the COF card) that regulate the spacing between the plates. The term "X-plate" refers to one of the two plates in a CROF card, wherein the spacers are fixed to this plate. More descriptions of the COF Card, CROF Card, and X-plate are given in the provisional application serial nos. 62/456,065, filed on Feb. 7, 2017, which is incorporated herein in its entirety for all purposes.

(2) Q-Card, Spacer and Uniform Sample Thickness

The devices, systems, and methods herein disclosed can include or use Q-cards, spacers, and uniform sample thickness embodiments for sample detection, analysis, and quantification. In some embodiments, the Q-card comprises spacers, which help to render at least part of the sample into a layer of high uniformity. The structure, material, function, variation and dimension of the spacers, as well as the uniformity of the spacers and the sample layer, are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, US Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

(3) Hinges, Opening Notches, Recessed Edge and Sliders

The devices, systems, and methods herein disclosed can include or use Q-cards for sample detection, analysis, and quantification. In some embodiments, the Q-card comprises hinges, notches, recesses, and sliders, which help to facilitate the manipulation of the Q card and the measurement of the samples. The structure, material, function, variation and dimension of the hinges, notches, recesses, and sliders are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

In some embodiments of QMAX, the sample contact area of one or both of the plates comprises a compressed open flow monitoring surface structures (MSS) that are configured to monitoring how much flow has occurred after COF. For examples, the MSS comprises, in some embodiments, shallow square array, which will cause friction to the components (e.g. blood cells in a blood) in a sample. By checking the distributions of some components of a sample, one can obtain information related to a flow, under a COF, of the sample and its components.

The depth of the MSS can be $1/1000$, $1/100$, $1/100$, $1/5$, $1/2$ of the spacer height or in a range of any two values, and in either protrusion or well form.

(4) Q-Card, Sliders, and Smartphone Detection System

The devices, systems, and methods herein disclosed can include or use Q-cards for sample detection, analysis, and quantification. In some embodiments, the Q-cards are used together with sliders that allow the card to be read by a smartphone detection system. The structure, material, function, variation, dimension and connection of the Q-card, the sliders, and the smartphone detection system are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

(5) Detection Methods

The devices, systems, and methods herein disclosed can include or be used in various types of detection methods. The detection methods are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

(6) Labels, Capture Agent and Detection Agent

The devices, systems, and methods herein disclosed can employ various types of labels, capture agents, and detection agents that are used for analytes detection. The labels are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

(7) Analytes

The devices, systems, and methods herein disclosed can be applied to manipulation and detection of various types of analytes (including biomarkers). The analytes and are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

(8) Applications (Field and Samples)

The devices, systems, and methods herein disclosed can be used for various applications (fields and samples). The applications are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

(9) Cloud

The devices, systems, and methods herein disclosed can employ cloud technology for data transfer, storage, and/or analysis. The related cloud technologies are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

Additional Notes

Further examples of inventive subject matter according to the present disclosure are described in the following enumerated paragraphs.

It must be noted that as used herein and in the appended claims, the singular forms "a", "an", and "the" include plural referents unless the context clearly dictates otherwise, e.g., when the word "single" is used. For example, reference to "an analyte" includes a single analyte and multiple analytes, reference to "a capture agent" includes a single capture agent and multiple capture agents, reference to "a detection agent" includes a single detection agent and multiple detection agents, and reference to "an agent" includes a single agent and multiple agents.

As used herein, the terms "adapted" and "configured" mean that the element, component, or other subject matter is designed and/or intended to perform a given function. Thus, the use of the terms "adapted" and "configured" should not be construed to mean that a given element, component, or other subject matter is simply "capable of" performing a given function. Similarly, subject matter that is recited as being configured to perform a particular function may additionally or alternatively be described as being operative to perform that function.

As used herein, the phrase, "for example," the phrase, "as an example," and/or simply the terms "example" and "exemplary" when used with reference to one or more components, features, details, structures, embodiments, and/or methods according to the present disclosure, are intended to convey that the described component, feature, detail, structure, embodiment, and/or method is an illustrative, non-exclusive example of components, features, details, structures, embodiments, and/or methods according to the present disclosure. Thus, the described component, feature, detail, structure, embodiment, and/or method is not intended to be limiting, required, or exclusive/exhaustive; and other components, features, details, structures, embodiments, and/or methods, including structurally and/or functionally similar and/or equivalent components, features, details, structures, embodiments, and/or methods, are also within the scope of the present disclosure.

As used herein, the phrases "at least one of" and "one or more of," in reference to a list of more than one entity, means any one or more of the entity in the list of entity, and is not limited to at least one of each and every entity specifically listed within the list of entity. For example, "at least one of A and B" (or, equivalently, "at least one of A or B," or, equivalently, "at least one of A and/or B") may refer to A alone, B alone, or the combination of A and B.

As used herein, the term "and/or" placed between a first entity and a second entity means one of (1) the first entity, (2) the second entity, and (3) the first entity and the second entity. Multiple entity listed with "and/or" should be construed in the same manner, i.e., "one or more" of the entity so conjoined. Other entity may optionally be present other than the entity specifically identified by the "and/or" clause, whether related or unrelated to those entities specifically identified.

Where numerical ranges are mentioned herein, the invention includes embodiments in which the endpoints are included, embodiments in which both endpoints are excluded, and embodiments in which one endpoint is included and the other is excluded. It should be assumed that both endpoints are included unless indicated otherwise. Furthermore, unless otherwise indicated or otherwise evident from the context and understanding of one of ordinary skill in the art.

In the event that any patents, patent applications, or other references are incorporated by reference herein and (1) define a term in a manner that is inconsistent with and/or (2) are otherwise inconsistent with, either the non-incorporated portion of the present disclosure or any of the other incorporated references, the non-incorporated portion of the present disclosure shall control, and the term or incorporated disclosure therein shall only control with respect to the reference in which the term is defined and/or the incorporated disclosure was present originally.

What is claimed is:

1. A device for assaying a sample using light, comprising: a first plate, a second plate, spacers, and a textured surface, wherein:
   (i) the plates are movable relative to each other into different configurations;
   (ii) one or both plates are flexible;
   (iii) the first plate is transparent to the light;
   (iv) the second plate has, on its inner surface, a textured structure for scattering the light illuminated on the surface;
   (v) the textured surface is a bumpy, wavy rough surface; and
   (vi) the spacers are fixed to the inner surface of one of the plates, and have a predetermined uniform height that is larger than the average roughness of the textured surface but smaller than 200 µm;
   wherein one of the configurations is an open configuration, in which: the two plates are partially or entirely separated apart, the spacing between the two plates is not regulated by the spacers, and the sample is deposited on one or both of the plates;
   wherein one of the configurations is a closed configuration, which is configured after the sample deposition in the open configuration, and in the closed configuration: at least part of the deposited sample is compressed by the two plates into a continuous layer.

2. An apparatus, comprising:
   a) the device of claim 1;
   b) a mobile computing device having a camera module;
   c) a light source, and
   d) an external lens.

3. A method for assaying a sample using light, comprising the steps of:
   a) obtaining a sample that contains or is suspected of containing an analyte;
   b) obtaining the device of claim 1;
   c) depositing the sample on one or both of the plates of the device when the plates are in the open configuration;
   d) bringing the two plates together and pressing the plates into the closed configuration so that the sample forms a thin layer between the two plates; and
   e) measuring, after step (d), an optical signal from the sample.

4. The device of claim 1, wherein the textured surface has an average roughness range of 2 µm to 5 µm.

5. The device of claim 1, wherein the textured surface is made of semi-opaque white material, and the transmissivity is 10%~30%.

6. The device of claim 1, wherein the texture on the textured surface is periodic.

7. The device of claim 1, wherein the textured surface is made of semi-opaque white material, and has a transmissivity of 10% to 30%.

8. The device of claim 1, wherein the textured surface is opaque white material or coated with reflective metal film, the metal film selected from aluminum, silver or gold.

9. The device of claim 1, wherein the textured surface is made of a highly reflectively opaque white material with reflectivity of at least 50%, 60%, 70%, 80%, 90%, 100%, or in a range between any of the two values.

10. The device of claim 1, wherein the reflection spectrum of the textured structure is within the range of 300 nm to 1000 nm.

11. The device of claim 1, wherein the texture surface is made of a semi-opaque white material, and has a transmissivity of 10%~30%.

12. The device of claim 1, wherein the texture surface is made of a reflective metal film.

13. The device of claim 1, wherein the textured surface has an arithmetic average roughness of 0.5 µm~200 µm, and a mean spacing of the asperities of >0.5 µm and an average slop of the profile is greater of 0.1.

14. The device of claim 1, wherein the textured surface is made of opaque white material.

15. The device of claim 1, wherein the average lateral feature size of the textured surface is at least 20% and up to 10-fold of the wavelength of the light, or in range between these two values.

16. The device of claim 1, wherein the average lateral feature size of the textured surface is at least 50% and up to 1000-fold of the wavelength of the light, or in range between these two values.

17. The device of claim 1, wherein the textured surface has a surface roughness at least 20% of the wavelength of the light.

18. The device of claim 1, wherein the flexible plate has the thickness of the flexible plate times the Young's modulus of the flexible plate in the range 60 to 750 GPa-µm, and wherein the fourth power of the inter-spacer-distance (ISD) divided by the thickness of the flexible plate (h) and the Young's modulus (E) of the flexible plate, $ISD^4/(hE)$, is equal to or less than $10^6$ µm$^3$/GPa.

19. The device of claim 1, wherein the spacer has a height of 30 µm or less.

20. The device of claim 1, further comprising one or more reagents on one of the plates.

21. The device of claim 1, wherein one or both plates further comprise a location marker, a scale marker, an image marker, or any combination of thereof.

22. The apparatus of claim 2, wherein the light source emits white light.

23. The apparatus of claim 2, wherein the distance between the plates and the camera module of the mobile computing device is in a range of 15 mm to 20 mm.

24. The apparatus of claim 2, wherein the external lens is put between the plates and the camera module, so that the sample between the plates is in a working distance of the camera module, and a focal length of the external lens is 12 to 18 mm, and the distance between the external lens and the camera module is no larger than 3 mm.

25. The apparatus of claim 2, wherein the distance between the light source and the plates is in a range of 5 mm to 10 mm.

26. The apparatus of claim 2, wherein the distance between the plates and the camera module is 5 to 10 mm.

27. The apparatus of claim 2, wherein the distance between the external lens is put between the plates and the camera module, so that the sample between the plates is in a working distance of the camera module, and a focal length of the external lens is 4 to 8 mm, and the distance between the external lens and the camera module is no larger than 3 mm.

28. The apparatus of claim 2, wherein the light source comprises an optical fiber guide that emits light from side and forms a ring shape.

29. The method of claim 3, wherein the optical signal is luminescence signal.

30. The method of claim 3, wherein the optical signal is colorimetric signal.

31. The method of claim 3, wherein the analyte is selected from the group of pH, ammonia, nitrite, nitrate, heavy metal, bacteria, lactose, food additive, and protein.

32. The method of claim 3, wherein the analyte is selected from the group consisting of glucose, albumin, sodium, potassium, chloride, urea nitrogen, creatinine, alkaline phosphatase, alanine amino transferase, aspartate amino transferase, bilirubin, cholesterol, triglycerides, hydrogen peroxide, and alcohol.

33. The method of claim 3, wherein the sample comprises a body fluid selected from the group consisting of: amniotic fluid, aqueous humour, vitreous humour, blood (e.g., whole blood, fractionated blood, plasma, serum, etc.), breast milk, cerebrospinal fluid (CSF), cerumen (earwax), chyle, chime, endolymph, perilymph, feces, gastric acid, gastric juice, lymph, mucus (including nasal drainage and phlegm), pericardial fluid, peritoneal fluid, pleural fluid, pus, rheum, saliva, sebum (skin oil), semen, sputum, sweat, synovial fluid, tears, vomit, urine and exhaled condensate.

34. The method of claim 3, wherein the sample comprises an environmental specimen that is obtained from: river, lake, pond, ocean, glaciers, icebergs, rain, snow, sewage, reservoirs, tap water, drinking water, soil, compost, sand, rocks, concrete, wood, brick, sewage; air, heat vents, industrial exhaust, or vehicular exhaust.

35. The method of claim 3, wherein the sample comprises a foodstuff specimen that includes: raw food ingredients, cooked or processed food, plant and animal sources of food, preprocessed food, or fully processed food.

\* \* \* \* \*